(12) United States Patent
Tischfield et al.

(10) Patent No.: US 9,938,575 B2
(45) Date of Patent: Apr. 10, 2018

(54) COMPOSITIONS AND METHODS FOR HIGH-THROUGHPUT NUCLEIC ACID ANALYSIS AND QUALITY CONTROL

(75) Inventors: Jay A. Tischfield, Martinsville, NJ (US); Andrew I. Brooks, New York, NY (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 13/814,619

(22) PCT Filed: Aug. 8, 2011

(86) PCT No.: PCT/US2011/046950
§ 371 (c)(1),
(2), (4) Date: Mar. 26, 2013

(87) PCT Pub. No.: WO2012/019190
PCT Pub. Date: Feb. 9, 2012

(65) Prior Publication Data
US 2013/0178376 A1    Jul. 11, 2013

Related U.S. Application Data

(60) Provisional application No. 61/371,354, filed on Aug. 6, 2010.

(51) Int. Cl.
*C12Q 1/68* (2006.01)
*C12Q 1/6876* (2018.01)

(52) U.S. Cl.
CPC ......... *C12Q 1/6876* (2013.01); *C12Q 1/6883* (2013.01); *C12Q 2600/156* (2013.01)

(58) Field of Classification Search
CPC .................................................. C12Q 1/68
USPC ........................................................ 506/7
See application file for complete search history.

(56) References Cited

U.S. PATENT DOCUMENTS

| | | | |
|---|---|---|---|
| 6,929,911 B2 * | 8/2005 | Oefner et al. ................. | 435/6.1 |
| 2006/0040262 A1 * | 2/2006 | Morris et al. ..................... | 435/6 |
| 2006/0292602 A1 | 12/2006 | Rivkees et al. | |
| 2007/0281896 A1 * | 12/2007 | Morris et al. ................... | 514/44 |
| 2008/0300147 A1 * | 12/2008 | Chegini et al. ................. | 506/16 |
| 2009/0099789 A1 * | 4/2009 | Stephan .................. | G06F 19/18 702/20 |
| 2009/0317817 A1 | 12/2009 | Oeth et al. | |
| 2010/0196879 A1 * | 8/2010 | Rivkees et al. .......... | C12Q 1/68 435/6 |

FOREIGN PATENT DOCUMENTS

| | | | |
|---|---|---|---|
| WO | WO 2009046021 A1 * | 4/2009 | |
| WO | WO 2010006215 A1 * | 1/2010 | |

OTHER PUBLICATIONS

Knauff et al., Genome-wide Association Study in Premature Ovarian Failure Patients Suggests ADAMTS19 as a Possible Candidate Gene, Human Reproduction, 2009, 24(9), 2772-2378.*
Knauff et al., Supplemental Tables S1 & S2, Genome-wide Association Study in Premature Ovarian Failure Patients Suggests ADAMTS19 as a Possible Candidate Gene, Human Reproduction, 2009, 24(9), 1-233.*
Score Results 20140520_112021_us-13-814-619-2.rng, 2014, 1.*
Score Results 20140520_112021_us-13-814-619-20.rng, 2014, 1.*
Score Results 20141209_055824_us-13-814-619-1.rnpbm, 2014, 1.*
Score Results 20141209_055824_us-13-814-619-10.rnpbm, 2014, 1.*
Score Results 20141216_112354_us-13-814-619-60.rnpbm, 2014, 1.*
Chow et al., Mass Spectrometric Detection of an SNP Panel As an Internal Positive Control for Fetal DNA Analysis in Maternal Plasma, Clinical Chemistry, 2007, 53(1), 141-142.*
Kosoy et al., Ancestry Informative Marker Sets for Determining Continenetal Origin and Admixture Proportions in Common Populations in America, Hum Mutat., 2009, 30(1), 69-78.*
Cross et al., Development of a Fingerprinting Panel Using Medically Relevant Polymorphisms, 2009, 2(17), 1-9.*
Tischfield et al., Poster Presentation, High-Throughput DNA Quality Control: Allelic Discrimination Panel for Determining Sample Contamination, Gender and Ethnicity in a Biorepository Setting, May 2010, 1.*
Poster Date: International Society for Biological & Environmental Repositories (ISBER) 2010 Annual Meeting & Exhibits, May 11-14, 2010, Rotterdam, The Netherlands, Poster QAC 16, High-Throughput DNA Quality Control Allelic Discriminatin Panel for Determining Sample Contamination, Gender and Ethnicity in a Biorespository Setting, 1-101 (see p. 77).*
Applied Biosystems, Product Bulletin TaqMan Genotyping Assays, Custom TaqMan SNP Genotyping Assays Simplify Your Genomic Projects, 2007, 1-4.*
Syvanen, Ann-Christine, Toward Genome-Wide SNP Genotyping, Nature Genetics, 2005, 37, S5-S10 (herein 1-11).*
Friedrich et al., DNA-Probes for the Highly Sensitive Identification of Single Nucleotide Polymorphism Using Single-Molecule Spectroscopy, 2007, 581, 1644-1648.*
Fluidgm, Specification Sheet, Biomark HD, 2004, 1-4.*
Chow et al. "Mass Spectrometic Detection of an SNP Panel as an Internal POsitive COntrol for Fetal DNA Analysis in Maternal Plasma." Clinical Chemistry. Jan. 2007 53(1):141-142.
National Center for Biotechnology Information SNP Database entry: rs1865680. Jan. 2, 2001.
National Center for Biotechnology Information SNP Database entry: rs525869. Jun. 29, 2003.
National Center for Biotechnology Information SNP Database entry: rs2058276. Jan. 29, 2001.
National Center for Biotechnology Information SNP Database entry: rs2040962. Jun. 29, 2003.
National Center for Biotechnology Information SNP Database entry: rs2032624. Jul. 18, 2005.
National Center for Biotechnology Information SNP Database entry: rs530501. Apr. 16, 2003.

* cited by examiner

*Primary Examiner* — Amy M Bunker
(74) *Attorney, Agent, or Firm* — Klarquist Sparkman, LLP

(57) ABSTRACT

Methods for improved quality control of nucleic acid containing biological samples utilized in high-throughput situations such as biorepositories engaged in the collection, processing, storage, distribution and analysis of such samples are disclosed.

19 Claims, 9 Drawing Sheets

| Source Plate | Fluidigm Plate | RUID | Upload Date | Project | DNA Source | Total Calls | Valid | Invalid | No Calls | Gender Adjusted | Result |
|---|---|---|---|---|---|---|---|---|---|---|---|
| 0004866-A01 | 1381314120 | SSC06485 | 2009-08-14 | SSC | WB | 96 | 93 | 0 | 3 | 0 | |
| 0004866-A02 | 1381314120 | SSC06441 | 2009-08-14 | SSC | WB | 96 | 93 | 0 | 3 | 0 | |
| 0004866-A03 | 1381314120 | SSC06434 | 2009-08-14 | SSC | WB | 96 | 96 | 0 | 0 | 0 | |
| 0004866-A04 | 1381314120 | SSC06513 | 2009-08-14 | SSC | WB | 96 | 96 | 0 | 0 | 0 | |
| 0004866-A05 | 1381314120 | SSC06429 | 2009-08-14 | SSC | WB | 96 | 93 | 0 | 3 | 0 | |
| 0004866-A06 | 1381314120 | SSC06416 | 2009-08-14 | SSC | WB | 96 | 96 | 0 | 0 | 0 | |
| 0004866-A07 | 1381314120 | SSC06426 | 2009-08-14 | SSC | WB | 96 | 96 | 0 | 0 | 0 | |
| 0004866-A08 | 1381314120 | K71740 | 2009-08-14 | NIDDK | WB | 96 | 93 | 0 | 3 | 0 | |
| 0004866-A09 | 1381314120 | 09NA41466 | 2009-08-14 | NIDA | WB | 96 | 96 | 0 | 0 | 0 | |
| 0004866-A10 | 1381314120 | CSH01267 | 2009-08-14 | CSH | WB | 96 | 93 | 0 | 3 | 0 | |
| 0004866-A11 | 1381314120 | NJT00470 | 2009-08-14 | NJT | WB | 96 | 96 | 0 | 0 | 0 | |
| 0004866-A12 | 1381314120 | MMRF0058 | 2009-08-14 | MMRF | WB | 96 | 96 | 0 | 0 | 0 | |
| 0004866-B01 | 1381314120 | SSC06482 | 2009-08-14 | SSC | WB | 96 | 93 | 0 | 3 | 0 | |
| 0004866-B02 | 1381314120 | SSC06439 | 2009-08-14 | SSC | WB | 96 | 93 | 0 | 3 | 0 | |

SEQUENCE LISTING

<160> NUMBER OF SEQ ID NOS: 106

<210> SEQ ID NO 1

```
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 1
actccagaac aagtgaaata cagcanacta tatctatagc tgtttaagat g          51

<210> SEQ ID NO 2
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 2
agtcacaatt ggcaagcaca cctacngcca atagctctga agtttcagtg c          51

<210> SEQ ID NO 3
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 3
agtgaatgcc atccgtatca cctgtngaag gttcacctat gactttactg t          51

<210> SEQ ID NO 4
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 4
tcacaaattg tattaaatca aaaaancttc gctgagtgct taccatgtgc c          51

<210> SEQ ID NO 5
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 5
gtatgattga tacatatcta attaanagct aatgaaaaaa atggcaatcc t          51
```

```
<210> SEQ ID NO 6
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or a

<400> SEQUENCE: 6
agaaactgtg aatagagaag tagccnttct tcttgctaag tttctttcag a         51

<210> SEQ ID NO 7
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 7
ctgtacaaat cagatgaagc ctgctnctct gaccacactg actatacgaa t         51

<210> SEQ ID NO 8
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 8
ctagtatgat ttgaacaaaa agttgngata ctggtatttt cagttggcca c         51

<210> SEQ ID NO 9
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 9
tctgttcagg tttctctcca tctctnttta ctcaggtcac aggaccttgg g         51

<210> SEQ ID NO 10
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or c

<400> SEQUENCE: 10
cttacaattc aagggcattt agaacncttt gtcatctgtt aatattcaga a         51
```

<210> SEQ ID NO 11
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 11
agattgtcat aactctggac gtatgnaagt gtagcatatg taaggccaga g    51

<210> SEQ ID NO 12
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 12
tgttttcctt ttgtgattcc acttcngtgt gaagcaagca gtgcttgttt t    51

<210> SEQ ID NO 13
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 13
aggggagagg acgcaggcat tacccncaac ctccagcacg gacacacagg g    51

<210> SEQ ID NO 14
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or a

<400> SEQUENCE: 14
gacatccagg tagctaaaat actgtnagtg agggacttag caagggagtc a    51

<210> SEQ ID NO 15
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 15
tgaaaagctt tagaagaaaa aagctntgtg gctattgagt ttggccagag t    51

```
<210> SEQ ID NO 16
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 16
ctcaatcccc cttaatgttt tcatcngctt cattcagaca cccatccttt a           51

<210> SEQ ID NO 17
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 17
acaattctat taaagccaat cctgangcta agtcctcacc tgaaagaagc g           51

<210> SEQ ID NO 18
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 18
aaaacatgtt tagggtttga agaatngcca agtacttcat aaatatggct t           51

<210> SEQ ID NO 19
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 19
actcaaccgt cttgacaact ctcatnccaa acaggtttgc accccccaatg g          51

<210> SEQ ID NO 20
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 20
```
ccagcaaaca tgtaaagtgt gagagntaaa taagaatata aaatcacaga a        51

<210> SEQ ID NO 21
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 21
gcctgcagtg agcattcaaa tcctcnagga acagggtggg gaggtgggac a        51

<210> SEQ ID NO 22
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 22
atgggctgta ccctcactat tggtgnttgt ctctgcaatt gatgtgctcc t        51

<210> SEQ ID NO 23
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 23
aaaatgagga aactaatgca taggcnagtt tcatccttat gtggcagaca g        51

<210> SEQ ID NO 24
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 24
taagagctga tttctgtgtc tgcctntcac actagacttc cacatcctta g        51

<210> SEQ ID NO 25
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 25

-continued gttaataatt tccactaaca acgcanaact caattagcat aataagcatt t          51

<210> SEQ ID NO 26
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 26
ggcaaattga cctgcttgtg ctcatngagg ctgggtagca gcagcagggt c          51

<210> SEQ ID NO 27
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 27
atagcatcta ccatcagccc aattcnaaag accatttatt taatcagcaa c          51

<210> SEQ ID NO 28
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 28
gtgtatggtt tctttgtggg attctntgtt gttggctgaa atcatttaag c          51

<210> SEQ ID NO 29
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 29
cacatacctg caagcacggg tatctntaca caaataagtt tatctgtcca a          51

<210> SEQ ID NO 30
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 30
cgggatgcgg gggagggagc aagccnagta acaaataaag caaatatcat c           51

<210> SEQ ID NO 31
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 31
ctgagattca cctctagtcc ctctgngcag cctcctggaa tactcagctg g           51

<210> SEQ ID NO 32
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 32
agtctgcaac aagatcttgt agggangcta tcgctggcta ttaggtgatc a           51

<210> SEQ ID NO 33
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 33
tgggttaatt ttgctcagag tatccngagt tagccactag gctgcgggtg a           51

<210> SEQ ID NO 34
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 34
ataaccttaa ctaagacaac aacccngacc aagaaaacat acttaagagc g           51

<210> SEQ ID NO 35
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 35
ataaatgggc tctttcccac aatgtnggac taactttctg tcagaaccac c         51

<210> SEQ ID NO 36
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 36
ccagggaaac atctagcatt tttctncaat gggactgagc tgcgaaattc a         51

<210> SEQ ID NO 37
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 37
tttttataag agaacaggga atactnaaac acacagagga gaagaccacg t         51

<210> SEQ ID NO 38
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 38
taagcaaaaa tgatcacgca ctacanactg ttaaactgtt catagcaact a         51

<210> SEQ ID NO 39
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 39
tgaacacatt tcaggaagtt gaattntatc ttggaaaaaa acagatttgg a         51

<210> SEQ ID NO 40
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26

<223> OTHER INFORMATION: n = c or t

<400> SEQUENCE: 40
atattctaag tgaaggagag aaaganttca aatgtttgta agcatggaag a    51

<210> SEQ ID NO 41
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 41
cagaaatgct gtggatattg acttancgga ccaagtttgg gatgggcaag t    51

<210> SEQ ID NO 42
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 42
acaggacagg acagttattc aggaanagct tggggacaat gcccctccct a    51

<210> SEQ ID NO 43
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 43
aaggcgttgc aggagttgcc cagggngtgg ggtcctccag cctcagtgaa g    51

<210> SEQ ID NO 44
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 44
gacattctcc ttcttctatc tgtatncctt actgcatttt tgcactgcag t    51

<210> SEQ ID NO 45
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or t

<400> SEQUENCE: 45
gtgtcaattt tgaccagata ttaaanctca caactctcta aacttccttg a        51

<210> SEQ ID NO 46
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 46
aatgcaaatt tcaccttctt caaatntaca actttcatga tcaaattcaa a        51

<210> SEQ ID NO 47
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 47
ctaccttggg tcatcaagat atttantttc cttttaaata ttttcctac a         51

<210> SEQ ID NO 48
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 48
agatatatct tagatgaagc aatagngtca agagtagaaa tttcagtagg a        51

<210> SEQ ID NO 49
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 49
gatgtctcat gtaccccgta aatatntata cacttactgt gtacccacaa a        51

<210> SEQ ID NO 50
<211> LENGTH: 51
<212> TYPE: DNA
<213> ORGANISM: Artificial Sequence
<220> FEATURE:
<223> OTHER INFORMATION: Synthetic Sequence
<220> FEATURE:

```
<221> NAME/KEY: misc_feature
<222> LOCATION: 26
<223> OTHER INFORMATION: n = a or g

<400> SEQUENCE: 50
gcggcgacgg caaggacgac ggtcgngcag cggcttcccg gatctagtgc a          51

<210> SEQ ID NO 51
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 51
gaaagagccg gctcacttaa gaaatnccaa gtggtattac gatgtcactc c          51

<210> SEQ ID NO 52
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 52
cttaacatag tgttatcatt ttgatncagc taagagaatt ccactcctaa g          51

<210> SEQ ID NO 53
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 53
aagttgcaat atggcaaaac ctgtangaga tacaatttgt gattccactg a          51

<210> SEQ ID NO 54
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 54
taatgcaccc tctccctgct tctatnttct gtgcccattg cagcatcaga c          51

<210> SEQ ID NO 55
<211> LENGTH: 51
<212> TYPE: DNA
<213> ORGANISM: Artificial Sequence
<220> FEATURE:
<223> OTHER INFORMATION: Synthetic Sequence
```

```
<220> FEATURE:
<221> NAME/KEY: misc_feature
<222> LOCATION: 26
<223> OTHER INFORMATION: n = a or g

<400> SEQUENCE: 55
taaacacaag atagaagcag actagncatt tagcgtttcc acacagacgt t            51

<210> SEQ ID NO 56
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 56
aataatattt gaacccttca aacagntatg tacacaggat gcttgtagta t            51

<210> SEQ ID NO 57
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or t

<400> SEQUENCE: 57
gtgtcaattt tgaccagata ttaaanctca caactctcta aacttccttg a            51

<210> SEQ ID NO 58
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 58
gcccaggaac ccaaggattg cttctnaagt ccaaagagag gattcacgtt c            51

<210> SEQ ID NO 59
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 59
aaatcttgtg ttcatatttt gctatntata cctaactttc tcaagttgcc t            51

<210> SEQ ID NO 60
<211> LENGTH: 51
<212> TYPE: DNA
<213> ORGANISM: Artificial Sequence
<220> FEATURE:
```

```
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 60
aagctcagaa agatccagaa aggccngaat gatggtccag aaccaagaca a          51

<210> SEQ ID NO 61
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or a

<400> SEQUENCE: 61
gaacggcaga caaagcctca cattangcat ctctttagta aagcatccag a          51

<210> SEQ ID NO 62
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 62
gtgagacagt tggacaagat gattcnggga atttttcaag ctcaaccaaa c          51

<210> SEQ ID NO 63
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 63
gatgatctac cttgcaggta taatgnttca agcatttgaa agagaatcaa g          51

<210> SEQ ID NO 64
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 64
cctgaaggtg atggaagcct tgcatntgtg tcttggtgcc atggggagcc t          51

<210> SEQ ID NO 65
<211> LENGTH: 51
<212> TYPE: DNA
<213> ORGANISM: Artificial Sequence
```

```
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 65
taagacgggt ttttatcagg acatanccccc cattgtaagg agaggagtat c          51

<210> SEQ ID NO 66
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 66
catagtgagg ggttagacct gcattnattt cagtctttca caatctttga c           51

<210> SEQ ID NO 67
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 67
ccaagggaac gtgaggaggc cacacntaca gctcaccaaa cacatcagcc g           51

<210> SEQ ID NO 68
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 68
attaatgtaa aaactgcaag tggttngtga tcaaaactcc aatgcacatg t           51

<210> SEQ ID NO 69
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 69
tgtcagcatt taaaaataaa accgantgcc acatttgcag aaaaagaaca a           51

<210> SEQ ID NO 70
<211> LENGTH: 51
<212> TYPE: DNA
```

<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or g

<400> SEQUENCE: 70
gcatattctt aaatccgtct tgactnagct tcatttgtga aatgaaggat t          51

<210> SEQ ID NO 71
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 71
ccctgcctcc cacaccagtt tctccngagt ggaaagactt tcatctcgca c          51

<210> SEQ ID NO 72
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 72
ggtcaagata tcagctttca cccgtnagga caggttagtg ttttcttca a           51

<210> SEQ ID NO 73
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 73
ctcaacaaat agtgctaaaa taaatngcta accactgagg gaaacacagt t          51

<210> SEQ ID NO 74
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 74
tggattctgt tctcttgatg tatttntcta tcttcacgtc aatactgcaa t          51

<210> SEQ ID NO 75
<211> LENGTH: 51

-continued

```
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 75
aacaccggga ggtccttgca gctccnagga agcagtttgc tgataactca g        51

<210> SEQ ID NO 76
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 76
aagcttaacc cctgggctat gacaangagt tgtgactccc tccatttctg t        51

<210> SEQ ID NO 77
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 77
gcagctattg ccatttttt ctcatncaca aaatcctgta tcctgagaat g         51

<210> SEQ ID NO 78
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 78
caggagctta ggagaaataa aatctnaatt tcttttcagg agatgtaaga g         51

<210> SEQ ID NO 79
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 79 ctaattttc ttatctttgt tttaanctga tgcttttca aattcattct t          51

<210> SEQ ID NO 80
```

```
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 80
caatggctcg tctatggtta gtctcncagc cacattctca gaactgctca a          51

<210> SEQ ID NO 81
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 81
gatacaggtt atctgtatta cattgngttt ttacctacct ttcttgcaca t          51

<210> SEQ ID NO 82
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = g or t

<400> SEQUENCE: 82
atttctttca gctcttgtca ttcagnttaa agagaaacca tttgacattc t          51

<210> SEQ ID NO 83
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 83
tctcttctct tcagtcatca gaagcnttta attaccagct ttctctaatt a          51

<210> SEQ ID NO 84
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 84
agagcagcac actgaggctt tatggnttgc cctgccacaa gtgaacaggt c          51
```

<210> SEQ ID NO 85
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 85
ctcttgtaga cagggccctc tatctntgtg gtgcatcctt tatatctcca t    51

<210> SEQ ID NO 86
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 86
tcagtatctc caagtcaggt caggtnaggt atgggacgga tgtggcagtg g    51

<210> SEQ ID NO 87
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 87
tcttgggggt cctgctccat gctgcnttac cccaatcccc atcctaaatt a    51

<210> SEQ ID NO 88
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = t or g

<400> SEQUENCE: 88
atgtcacctt taggcagagg catttntatt attgttagtg gagctgctga g    51

<210> SEQ ID NO 89
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 89
tgaactgcgc tcctggatct tttacntaac tgtggttttt cacaaggttc t    51

<210> SEQ ID NO 90
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or t

<400> SEQUENCE: 90
cacttaacag gctctctttc cacccntgta gaaatacaaa aataagactt a      51

<210> SEQ ID NO 91
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 91
gactaaattg ttgaacactg gttacngtgc taggtattta caaacttgct c      51

<210> SEQ ID NO 92
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 92
attccagata gagctaaaac tgaagntttc cttatagaga tttatcctag t      51

<210> SEQ ID NO 93
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = t or g

<400> SEQUENCE: 93
attcactaaa catacatttg tatttncagt cttctgcttt atctttggaa a      51

<210> SEQ ID NO 94
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 94
tcactatatg ttggccttga ttggtnttcc tgaagtcttt tgggcatttc t      51

<210> SEQ ID NO 95
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 95
tccagccctt gtcccaaacg tgtgtntgca caggcacacg aaagaaggtg a          51

<210> SEQ ID NO 96
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 96
cccagttgtc agctctctga tctccngcaa tctgggactg gttcctgaac t          51

<210> SEQ ID NO 97
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 97
aatgtgccct agggcaagag agtaanttca cagcatgaag gtatcaatgg a          51

<210> SEQ ID NO 98
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or c

<400> SEQUENCE: 98
ggttaagcaa aaaagaaca attaantcac agttcagaga cctccaggag t           51

<210> SEQ ID NO 99
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or c

<400> SEQUENCE: 99
aggttggcag ccacagcaat agactnccac tagaagtcta gaagatgccc a               51

<210> SEQ ID NO 100
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 100
tttctggatg tgatgactgg caatgnggca gccatttgag ccttagggag c               51

<210> SEQ ID NO 101
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 101
aggggtttgc agaggcacag tgaaanaagg tgccgagaaa atagcagggg a               51

<210> SEQ ID NO 102
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = t or g

<400> SEQUENCE: 102
atgcaccatg gccatttgga actggntagt gagaggctgc cctgtccatt g               51

<210> SEQ ID NO 103
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = c or t

<400> SEQUENCE: 103
ggttatcatg gctgccctct cacttnttca gagacatgtg tttctaaggt c               51

<210> SEQ ID NO 104
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 104

```
gatggcttaa ctctatagaa aggaanagaa gctcagctta ttcatatgca a            51

<210> SEQ ID NO 105
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = a or g

<400> SEQUENCE: 105
ttacaaaaca tttttgcatt agcttnagaa ggataaacca attccatgct g            51

<210> SEQ ID NO 106
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: 26
<223> OTHER INFORMATION: n = t or g

<400> SEQUENCE: 106
agccaagaag ccaaggacag ctaatnctta gcacctggtt acagatgcct c            51
```

COMPOSITIONS AND METHODS FOR HIGH-THROUGHPUT NUCLEIC ACID ANALYSIS AND QUALITY CONTROL

This application is a § 371 national phase entry of PCT/US2011/046950 filed Aug. 8, 2011 claims priority to U.S. Provisional Application 61/374,354 filed Aug. 6, 2010, the entire contents being incorporated herein by reference as though set forth in full.

The United States government has rights in this invention which was made using funds from NIH Grant No. 5U24MH068457.

FIELD OF THE INVENTION

The present invention relates to the field of biorepositories, molecular biology and characterization of nucleic acids obtained from biological samples. More specifically, the invention provides compositions and methods to quantitatively and qualitatively assess the quality and integrity of genomic nucleic acid samples and further provides the means to standardize functional assessment of such nucleic acids for downstream applications.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

A biorepository is a data and biological materials repository that collects, processes, stores, and distributes data, biological samples or specimens to support scientific investigation. Biorepositories can contain or manage samples or specimens from animals, including humans, and other living organisms. Vertebrates, invertebrates, arthropods, plants and other life-forms are just a few of the many classes of living organisms which can be studied by preserving and storing samples taken. Generally, the purpose of a biorepository is to maintain data and biological specimens for future use in a state closely matching the original in vivo state. The four main operations of a biorepository are (i) collection or accession, (ii) processing, (iii) storage or inventory, and (iv) distribution of biological samples or specimens.

The quality of genomic DNA (gDNA) is a core component for all tissue, nucleic acid, and cell biorepository programs. To date, many different techniques have been used for assessing gDNA, however, no standard approach is presently in place for ensuring DNA quality for downstream applications. Currently, most gDNA quality measurements use non-specific assays which demonstrate the global quality of nucleic acid but provide little or no information on gender mismatches, potential sample contamination or ethnicity which are important metrics for any lab reposing or managing samples in a repository setting. Presently, most laboratories use gDNA for discovery applications that involve analysis via single nucleotide polymorphism (SNP) genotyping and Next Generation sequencing technologies, both of which have a polymerase chain reaction (PCR) component to their workflow.

Laboratory services are an essential component to most all biorepositories. Each process must have the appropriate workflow, analytical and functional quality control (QC) measures to ensure that the biologicals being extracted, stored and managed are of the highest quality.

There remains an unmet need for a standardized method for ensuring high quality of nucleic acids stored in such repositories as well as methods of analyzing such nucleic acids in downstream applications including and not limited to high-throughput whole genome and transcriptome analyses.

SUMMARY OF THE INVENTION

The present invention provides a collection of genetic markers for assessing quality and integrity of a nucleic acid sample. In one embodiment, the collection comprises at least 5 of the single nucleotide polymorphism (SNP)-containing nucleic acids set forth in Table 2 and having SEQ ID NOs: 1-106. In a particular embodiment, the collection comprises SEQ ID NOS: 1-106 or 1-96. The sequences of the SNP-containing nucleotide sequences may optionally be stored in a computer readable storage medium. In further embodiments, the SNP-containing nucleic acids are affixed to a solid support. In some embodiments, the SNPs are hu98Y, hu103X, hu106Y, hu107X, hu109X and hu111Y.

The present invention also provides a method for assessing the quality and integrity of a nucleic acid sample. An exemplary method comprises a) subjecting the nucleic acid sample to genotype analysis for each of the genetic markers in a collection of the invention, thereby confirming the presence or absence of said markers in said sample; and b) confirming that no discrepancy exists between previously determined markers and those identified in step a) wherein at least one discrepancy between the genotype analysis information of step a) and the previously determined markers for the sample is indicative of poor quality and integrity of the nucleic acid sample.

In one aspect, the nucleic acid sample is DNA selected from the group consisting of gDNA, cDNA, and recombinant DNA. The markers presented herein are indicative of a characteristic selected from the group consisting of gender, ethnicity and uniqueness. In certain embodiments, the genotype information is stored on a computer readable medium and the analysis is performed using a computer data base. The methods may also comprise preparation of a report of the analysis listing the characteristics identified.

The present invention also provides a method for assessing the gender of the source of a nucleic acid sample, said method comprising subjecting the nucleic acid sample to genotype analysis to generate a call for each of the genetic markers in a collection of the invention, wherein the source is assessed as male if a call is generated for a) all of hu103X, hu107X, hu109X, hu98Y, hu106Y and hu111Y, b) all of hu103X, hu107X and hu109X, and at least two of hu98Y, hu106Y and hu111Y, or c) at least two of hu103X, hu107X and hu109X, and all of hu98Y, hu106Y and hu111Y; and wherein the source is assessed as female if a) no call is generated for hu98Y, hu106Y or hu111Y, and b) a call is generated for at least two of hu103X, hu107X and hu109X.

The present invention also provides, a method for assessing the uniqueness of a first nucleic acid sample in a plurality of nucleic acid samples. An exemplary method comprises a) subjecting the first sample and the remaining plurality of samples to genotype analysis for each of the genetic markers in a collection of the invention, and b) comparing the genotype analysis information of step a) for the first sample with the genotype analysis information of step a) for the remaining plurality of samples, wherein at least one discrepancy between the genotype analysis information of step a) between the first sample and the remaining plurality of samples is indicative of the uniqueness of the first nucleic acid sample. In some embodiments, the genotype information is stored on a computer readable medium. In particular embodiments, the nucleic acid sample is DNA selected from the group consisting of gDNA, cDNA, and recombinant DNA.

The present invention also provides a method for assessing the quality of a nucleic acid sample. This method comprises subjecting the sample to genotype analysis to generate a call for each of the genetic markers in a collection of the invention, wherein failure to generate a call for at least three of the genetic markers in the collection is indicative of poor quality of the nucleic acid sample.

BRIEF DESCRIPTION OF THE DRAWINGS

FIG. 2A provides exemplary data using the hu31 SNP and FIG. 2B shows an exemplary array of gender determination using the hu106Y SNP.

FIG. 3A is an illustration of 9200 signals generated on a single 96.96 Fluidigm array. Call rates exceed 99.8% for the RUCDR QC panel. FIG. 3B is a scatter plot of all 96 QC assays on the Fluidigm array. All individual assays have segregation across experimental samples for both gender and autosomal assays.

DETAILED DESCRIPTION OF THE INVENTION

Figure 1:
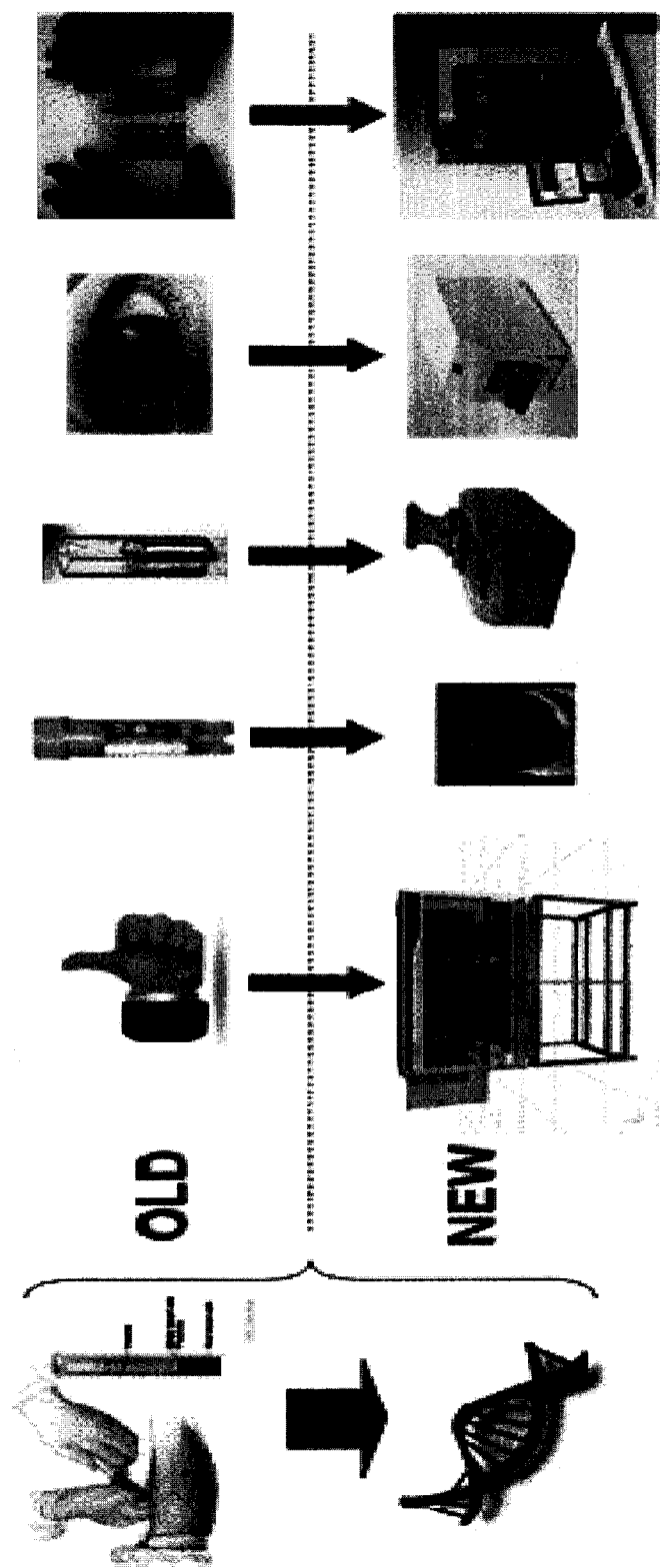
FIG. 1 illustrates comparison between the old and new methods for DNA handling and quality control workflows.

The Rutgers University Cell and DNA Repository (RUCDR) has implemented a new, fully automated DNA workflow which is inclusive of nucleic acid extraction, sample transfer, analytical and functional QC and sample storage. This approach combines sophisticated and accurate liquid handling capabilities, automated extraction technologies, state of the art storage formats which maximize freezer space consumption and most importantly improved analytical and functional quality control of all nucleic acid samples. The QC workflow employs non-contact volume measurements, high-throughput cuvetteless spectroscopy and high-throughput single nucleotide polymorphisms (SNP) analysis to validate sample quality as a function of downstream applications, control for contamination during processing, and generate molecular fingerprints for gender and ethnicity for all repository samples.

The present invention provides a rapid, cost effective means for assessing the quality of the nucleic acid in a sample, while capturing critical information on each sample tested. In particular embodiments, the nucleic acid in the sample is genomic DNA (gDNA). We have developed a panel of 96 or 106 SNPs and have validated the panel using the Fluidigm 96.96 dynamic array for the efficient and cost effective processing of samples.

The panel has been used to effectively determine sample contamination (at the time of extraction and/or cell line immortalization), to decipher reported gender status for genotyping studies, and the determination of ethnicity information for each gDNA. The flexibility of the Fluidigm dynamic array allows for rapid QC testing while retaining the flexibility that is needed for other specific supplementary panels in order to generate more in depth information on ethnicity (126 SNPs) and paternity (136 SNPs) analysis as needed. The correlation of the Fluidigm BioMark™ genotyping system to our standard quantitative polymerase chain reaction (QPCR) validation of all assays utilized is 100%. The correlation to SNP data from DNA microarray and capillary electrophoresis analysis is 100%. This approach allows the repository to easily quality control over 10,000 samples per month while reducing operating costs and generating essential information that is used for sample and study management. The RUCDR QC database is used to validate GWAS (genome-wide association study) data in the event of a discrepancy given >90% of SNPs in this panel are represented on a variety of commercial array platforms. The present invention provides methods for the selection of SNPs for the QC panel, standard operating procedures for sample processing, and an analysis schema for the rapid processing of genotyping data for quality assessment.

The following definitions are provided to facilitate the understanding of the present invention.

A "single nucleotide polymorphism (SNP)" refers to a change in which a single base in the DNA differs from the usual base at that position. These single base changes are called SNPs or "snips." Millions of SNPs have been cataloged in the human genome. Some SNPs, such as those which cause and modify the severity of sickle cell anemia are responsible for disease. Other SNPs are normal variations in the genome.

"Ancestry-informative markers" (AIMs) are genetic markers with large allele frequency differentials between populations from different geographical regions. AIMs can be used to estimate the geographical origins of the ancestors of an individual and to ascertain what proportion of ancestry is derived from each geographical region. Large collections of AIMs more or less evenly spaced across the genome can be used to discover novel genes underlying complex diseases in a technique called admixture mapping or mapping by admixture linkage disequilibrium. Many AIMs are known in the art, thus providing a large number of AIMs to choose from when selecting AIMs for the preparation of genetic marker panels for specific analyses. In a particular embodiment of the invention, a panel of the first 96 or all of the 106 SNPs is shown in Table 1, which includes a particular selection of AIMs.

A "genome-wide association marker" is a genetic marker of an observable trait. Typically a genome-wide association marker is identified in a genome-wide association study, which is an examination of genetic variation across a given genome, designed to identify genetic associations with observable traits. In human studies, such traits can include, for example, blood pressure, weight, risk and protective factors for diseases or conditions such as asthma, cancer, diabetes, heart disease, mental illness.

A "genetic marker" is a gene or nucleic acid sequence, often with a known location on a chromosome, which can be used to identify cells, individuals or species. It can be described as a variation, which may arise due to mutation or alteration in the genomic loci, which can be observed. A genetic marker may be a short nucleic acid sequence, such as a sequence surrounding a single base-pair change (single nucleotide polymorphism, SNP), or a long one, such as microsatellites.

Commonly used types of genetic markers include, but are not limited to, RFLP (restriction fragment length polymorphism), AFLP (amplified fragment length polymorphism), RAPD (random amplification of polymorphic DNA), VNTR (variable number tandem repeat), microsatellite polymorphism, SSR (or simple sequence repeat), SNP (or single nucleotide polymorphism), STR (short tandem repeat), and SFP (single feature polymorphism).

The terms "solid support" or "support", as used herein are used interchangeably and refer to a material or group of materials having a rigid or semi-rigid surface or surfaces. In many embodiments, at least one surface of the solid support will be substantially flat, although in some embodiments it may be desirable to physically separate regions with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary supports.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The terms "sample" and "nucleic acid sample" refer to any sample containing nucleic acid material. The nucleic acid material can be DNA, including gDNA, cDNA, free floating DNA and recombinant DNA, or RNA, including mRNA, miRNA and total RNA. In particular embodiments, the nucleic acid sample is DNA, more particularly gDNA.

"Target nucleic acid" as used herein refers to a previously defined region of a nucleic acid present in a complex nucleic acid mixture wherein the defined wild-type region contains at least one known nucleotide variation which is associated with a particular genetic phenotype, trait, or occurs rarely.

Samples can be isolated or derived from any "source" that contains or is believed to contain a nucleic acid. In particular embodiments, the sample is isolated or derived from an individual, for example a patient in a clinical study, and can come from any living source including human and non-human organisms, including plants. For example, individuals may include humans and other mammals, such as bovines, equines, ovines, canines, or felines. In particular embodiments, samples come from humans. The sample may be of any biological tissue or fluid. The sample may be a clinical sample, which is a sample derived from a patient. Such samples include, but are not limited to, sputum, blood, blood cells, amniotic fluid, plasma, semen, bone marrow, tissue or fine needle biopsy samples, urine, peritoneal fluid, and pleural fluid, or cells or cellular extracts there from. Samples may also include sections of tissues such as frozen sections taken for histological purposes. In some embodiments, samples may be isolated or derived from recombinant cells, cellular lysates or extracts, or in vitro reaction mixtures.

The "quality and integrity" of a nucleic acid sample refers to the condition of the nucleic acid in the sample and to the accurate identification of the sample. Quality and integrity are reflected by a number of detectable characteristics of the sample. Issues of importance and concern to a biorepository that collects or acquires, processes, stores, distributes and analyzes large numbers of biological nucleic acid containing samples are sample degradation, gender misidentification or mismatches, ethnicity misidentification or mismatches, sample contamination, sample mislabeling, errors in data capture. The methods of the present invention allow for the detection of problems with regard to the quality and integrity of a nucleic acid sample by examination of particular genetic markers in the sample. In particular embodiments, markers reflective of gender and/or ethnicity and/or uniqueness are used to detect discrepancies with input information about a sample. In particular embodiments, the methods of the invention are used to confirm the gender and/or ethnicity of the source of the nucleic acid sample. In particular embodiments, the methods of the invention are used to ascertain or confirm whether a nucleic acid sample has been contaminated with, for example, a sample from another source, mislabeled, or whether data or information associated with a particular nucleic acid sample has been improperly or incorrectly recorded.

The term "genotyping" refers to the determination of the genetic information an individual carries at one or more positions in the genome. For example, genotyping my comprise the determination of which allele or alleles an individual carries for a single SNP or the determination of which allele or alleles an individual carries for a plurality of SNPs. For example, a particular nucleotide in a genome may be a T in some individuals and a C in other individuals. Those individuals who have a T at the position have the T allele and those who have a C have the C allele. In a diploid organism the individual will have two copies of the sequence containing the polymorphic position so the individual may have a T allele and a C allele or alternatively two copies of the T allele or two copies of the C allele. Those individuals who have two copies of the C allele are homozygous for the C allele, those individuals who have two copies of the T allele are homozygous for the T allele, and those individuals who have one copy of each allele are heterozygous. The alleles are often referred to as the A allele, often the major allele, and the B allele, often the minor allele. The genotypes may be AA (homozygous A), BB (homozygous B) or AB (heterozygous). Genotyping methods generally provide for identification of the sample as AA, BB or AB.

As used herein the term "call" or "calls" refers to genotype assignment or designation of a particular characteristic to a sample. For example, in genotype calling related to SNPs, a genotype "call" or assignment is made (i.e., AA, AB or BB genotype for the two alleles).

Methods of Using the SNP Panel of the Invention in Quality Control and DNA Characterization Assays A panel of 106 SNPs (a SNP quality control panel) was developed as the main functional component of this quality control schema (see Table 1). SNPs were selected based on criteria that include: A) representation of the genome, B) markers in polymorphic regions to confer unique identity to each sample, C) selection of ancestry markers (ancestry-informative markers (AIMs)) to determine ethnicity, D) selection of SNPs to confirm gender determination, E) selection of SNPs represented on commercial array based platforms to use as verification markers for GWAS. This panel was developed and implemented on the Fluidigm BioMark™ genotyping system allowing for the analysis of over 10,000 unique samples per month.

Table 1 presents the panel of SNPs used for analytical and functional quality control. The "RUID" column indicates the Rutgers University identification number for each SNP. The "dbSNP" column indicates the NCBI database single nucleotide polymorphism reference number for each SNP. SNPs have been categorized as indicated in the "Category" column to distinguish their use in analyses. The categories were as follows: I=SNP represented on the Illumina Human1M-Duo arrays and Human1M Quad Arrays and; A=SNP represented on the Affymetrix Genome-Wide Human SNP Array 6.0; A/I=SNP represented on both Illumina and Affymetrix array platforms; P=highly polymorphic SNPs used to confer pattern or profile uniqueness; G=gender determination; E=ethnicity determination.

Table 2 presents the actual single nucleotide polymorphic change for each of the 96 SNPs of the RUID panel, in the context of their respective surrounding nucleic acid sequences (SEQ ID NOs: 1-96). The "Assay ID" number identifies the Applied Biosystems commercial TaqMan assay that detects the SNP described in Table 2.

TABLE 1

Panel of SNPs used for analytical and functional quality control.

| RUID | dbSNP | Category |
|---|---|---|
| hu1 | rs1471939 | I, E |
| hu2 | rs4666200 | I, E |
| hu3 | rs7554936 | I |
| hu4 | rs9530435 | A, I, E |
| hu5 | rs6104567 | I, E |
| hu7 | rs2272998 | P |
| hu9 | rs560681 | A, I, E |
| hu11 | rs6591147 | A, I, E |
| hu12 | rs321198 | P |
| hu13 | rs3784230 | I, E |
| hu14 | rs870347 | I, E |
| hu15 | rs2946788 | I, E |
| hu16 | rs4891825 | I, E |

TABLE 1-continued

Panel of SNPs used for analytical and functional quality control.

| RUID | dbSNP | Category |
|---|---|---|
| hu17 | rs10108270 | A, I, E |
| hu18 | rs2397060 | A, I, E |
| hu20 | rs7229946 | A, E |
| hu21 | rs13182883 | A, I, E |
| hu22 | rs1876482 | P |
| hu23 | rs315791 | A, I, E |
| hu24 | rs7205345 | P |
| hu25 | rs798443 | A, I, E |
| hu26 | rs4717865 | A, I, E |
| hu27 | rs2416791 | A, I, E |
| hu28 | rs2125345 | A, I |
| hu29 | rs4746136 | A, I, E |
| hu30 | rs4821004 | A, I, E |
| hu31 | rs13218440 | I, E |
| hu32 | rs1523537 | I, E |
| hu33 | rs1058083 | I, E |
| hu34 | rs1344870 | I, E |
| hu35 | rs7704770 | I, E |
| hu36 | rs1410059 | A, I, E |
| hu37 | rs5768007 | I, E |
| hu38 | rs260690 | A, I, E |
| hu39 | rs13400937 | I, E |
| hu41 | rs4918842 | A, I, E |
| hu42 | rs9809104 | I, E |
| hu43 | rs2073383 | P |
| hu44 | rs1821380 | P |
| hu45 | rs279844 | P |
| hu46 | rs952718 | P |
| hu47 | rs447818 | P |
| hu48 | rs13134862 | P |
| hu49 | rs4463276 | I, E |
| hu50 | rs9845457 | I, E |
| hu51 | rs3943253 | I |
| hu52 | rs6548616 | A, I, E |
| hu53 | rs731257 | A, I, E |
| hu54 | rs9319336 | I, E |
| hu55 | rs1019029 | I, E |
| hu56 | rs1358856 | P |
| hu57 | rs279844 | P |
| hu58 | rs1823718 | I, E |
| hu59 | rs2503107 | I, E |
| hu61 | rs10236187 | A, I, E |
| hu62 | rs1513181 | I, E |
| hu63 | rs7657799 | A, I, E |
| hu64 | rs2504853 | A, I, E |
| hu65 | rs772262 | I |
| hu66 | rs3737576 | I, E |
| hu67 | rs7520386 | P |
| hu68 | rs445251 | P |
| hu69 | rs10488710 | A, E |
| hu70 | rs722869 | P |
| hu71 | rs1109037 | A, E |
| hu72 | rs3780962 | I, E |
| hu73 | rs7997709 | I, E |
| hu74 | rs4670767 | I, E |
| hu75 | rs9522149 | I, E |
| hu76 | rs4908343 | A, I, E |
| hu77 | rs6451722 | I, E |
| hu78 | rs12629908 | I, E |
| hu79 | Rs1336071 | A, E |
| hu80 | Rs740598 | P |
| hu81 | Rs12997453 | I |
| hu82 | Rs2352476 | P |
| hu83 | Rs1554472 | A, I, E |
| hu84 | rs10007810 | I |
| hu85 | rs1760921 | I, E |
| hu86 | rs1040045 | I, E |
| hu87 | rs10496971 | A, I, E |
| hu88 | rs7803075 | A, I, E |
| hu89 | rs987640 | P |
| hu90 | rs6444724 | I, E |
| hu91 | rs10092491 | I, E |
| hu92 | rs735612 | A, E |
| hu93 | rs985492 | A, I |
| hu94 | rs338882 | I, E |
| hu95 | rs9951171 | P |

TABLE 1-continued

Panel of SNPs used for analytical and functional quality control.

| RUID | dbSNP | Category |
|---|---|---|
| hu96 | rs3907047 | A, I, E |
| hu98Y | rs1865680 | G |
| hu103X | rs525869 | G |
| hu106Y | rs2058276 | G |
| hu107X | rs2040962 | G |
| hu109X | rs530501 | G |
| hu111Y | rs2032624 | G |
| hu113 | rs734873 | P, E |
| hu114 | rs2357442 | P, E |

TABLE 1-continued

Panel of SNPs used for analytical and functional quality control.

| RUID | dbSNP | Category |
|---|---|---|
| hu115 | rs1296819 | P, E |
| hu116 | rs2835370 | P, E |
| hu117 | rs3745099 | P, E |
| hu118 | rs200354 | P, E |
| hu119 | rs3793451 | P, E |
| hu120 | rs2030763 | P, E |
| hu121 | rs10510228 | P, E |
| hu122 | rs946918 | P, E |

TABLE 2

SNPs in Context of Surrounding Sequence.

| RUID | Assay ID | Context Sequence | SEQ ID NO |
|---|---|---|---|
| hu1 | C__8793707_20 | ACTCCAGAACAAGTGAAATACAGCA[C/T]ACTATATCTATAGCTGTTTAAGATG | 1 |
| hu2 | C_27891561_10 | AGTCACAATTGGCAAGCACACCTAC[A/G]GCCAATAGCTCTGAAGTTTCAGTGC | 2 |
| hu3 | C_26139689_10 | AGTGAATGCCATCCGTATCACCTGT[C/T]GAAGGTTCACCTATGACTTTACTGT | 3 |
| hu4 | C_27192660_10 | TCACAAATTGTATTAAATCAAAAAA[C/T]CTTCGCTGAGTGCTTACCATGTGCC | 4 |
| hu5 | C_30147358_10 | GTATGATTGATACATATCTAATTAA[G/T]AGCTAATGAAAAAAATGGCAATCCT | 5 |
| hu98Y | C_27096147_20 | AGAAACTGTGAATAGAGAAGTAGCC[G/A]TTCTTCTTGCTAAGTTTCTTTCAGA | 6 |
| hu7 | C__1256256_1_ | CTGTACAAATCAGATGAAGCCTGCT[C/G]CTCTGACCACACTGACTATACGAAT | 7 |
| hu106Y | C_11963580_10 | CTAGTATGATTTGAACAAAAAGTTG[C/T]GATACTGGTATTTTCAGTTGGCCAC | 8 |
| hu9 | C__1006721_1_ | TCTGTTCAGGTTTCTCTCCATCTCT[A/G]TTTACTCAGGTCACAGGACCTTGGG | 9 |
| hu111Y | C__2292796_20 | CTTACAATTCAAGGGCATTTAGAAC[A/C]CTTTGTCATCTGTTAATATTCAGAA | 10 |
| hu11 | C__1636106_10 | AGATTGTCATAACTCTGGACGTATG[C/T]AAGTGTAGCATATGTAAGGCCAGAG | 11 |
| hu12 | C__3004178_10 | TGTTTTCCTTTTGTGATTCCACTTC[C/T]GTGTGAAGCAAGCAGTGCTTGTTTT | 12 |
| hu13 | C__2770233_10 | AGGGGAGAGGACGCAGGCATTACCC[A/G]CAACCTCCAGCACGGACACACAGGG | 13 |
| hu14 | C__3052139_10 | GACATCCAGGTAGCTAAAATACTGT[A/C]AGTGAGGGACTTAGCAAGGGAGTCA | 14 |
| hu15 | C___302128_10 | TGAAAAGCTTTAGAAGAAAAAAGCT[G/T]TGTGGCTATTGAGTTTGGCCAGAGT | 15 |
| hu16 | C_27956007_10 | CTCAATCCCCCTTAATGTTTTCATC[A/G]GCTTCATTCAGACACCCATCCTTTA | 16 |
| hu17 | C_30263561_10 | ACAATTCTATTAAAGCCAATCCTGA[A/C]GCTAAGTCCTCACCTGAAAGAAGCG | 17 |
| hu18 | C_16226232_10 | AAAACATGTTTAGGGTTTGAAGAAT[C/T]GCCAAGTACTTCATAAATATGGCTT | 18 |
| hu103X | C__2808317_10 | ACTCAACCGTCTTGACAACTCTCAT[C/T]CCAAACAGGTTTGCACCCCAATGG | 19 |
| hu20 | C___105475_10 | CCAGCAAACATGTAAAGTGTGAGAG[A/G]TAAATAAGAATATAAAATCACAGAA | 20 |
| hu21 | C__2556113_10 | GCCTGCAGTGAGCATTCAAATCCTC[A/G]AGGAACAGGGTGGGAGGTGGGACA | 21 |
| hu22 | C_11640969_10 | ATGGGCTGTACCCTCACTATTGGTG[A/G]TTGTCTCTGCAATTGATGTGCTCCT | 22 |
| hu23 | C__3032822_1_ | AAAATGAGGAAACTAATGCATAGGC[A/C]AGTTTCATCCTTATGTGGCAGACAG | 23 |
| hu24 | C_31419546_10 | TAAGAGCTGATTTCTGTGTCTGCCT[C/G]TCACACTAGACTTCCACATCCTTAG | 24 |
| hu25 | C__8914321_10 | GTTAATAATTTCCACTAACAACGCA[A/G]AACTCAATTAGCATAATAAGCATTT | 25 |
| hu26 | C_11448835_10 | GGCAAATTGACCTGCTTGTGCTCAT[A/G]GAGGCTGGGTAGCAGCAGCAGGGTC | 26 |
| hu27 | C_16234767_10 | ATAGCATCTACCATCAGCCCAATTC[A/G]AAAGACCATTTATTTAATCAGCAAC | 27 |
| hu28 | C_15885530_10 | GTGTATGGTTTCTTTGTGGGATTCT[C/T]TGTTGTTGGCTGAAATCATTTAAGC | 28 |
| hu29 | C_27913671_10 | CACATACCTGCAAGCACGGGTATCT[A/G]TACACAAATAAGTTTATCTGTCCAA | 29 |

TABLE 2-continued

SNPs in Context of Surrounding Sequence.

| RUID | Assay ID | Context Sequence | SEQ ID NO |
|---|---|---|---|
| hu30 | C__2465604_1_ | CGGGATGCGGGGGAGGGAGCAAGCC[C/T]AGTAACAAATAAAGCAAATATCATC | 30 |
| hu31 | C__9371416_10 | CTGAGATTCACCTCTAGTCCCTCTG[A/G]GCAGCCTCCTGGAATACTCAGCTGG | 31 |
| hu32 | C__2508482_10 | AGTCTGCAACAAGATCTTGTAGGGA[C/T]GCTATCGCTGGCTATTAGGTGATCA | 32 |
| hu33 | C__1619935_1_ | TGGGTTAATTTTGCTCAGAGTATCC[A/G]GAGTTAGCCACTAGGCTGCGGGTGA | 33 |
| hu34 | C__8767848_10 | ATAACCTTAACTAAGACAACAACCC[G/T]GACCAAGAAAACATACTTAAGAGCG | 34 |
| hu35 | C__1995608_10 | ATAAATGGCTCTTTCCCACAATGT[A/G]GGACTAACTTTCTGTCAGAACCACC | 35 |
| hu36 | C__7538108_10 | CCAGGGAAACATCTAGCATTTTTCT[C/T]CAATGGGACTGAGCTGCGAAATTCA | 36 |
| hu37 | C_29548230_10 | TTTTTATAAGAGAACAGGGAATACT[C/T]AAACACACAGAGGAGAAGACCACGT | 37 |
| hu38 | C___790944_10 | TAAGCAAAATGATCACGCACTACA[A/C]ACTGTTAAACTGTTCATAGCAACTA | 38 |
| hu39 | C_32187474_20 | TGAACACATTTCAGGAAGTTGAATT[G/T]TATCTTGGAAAAAAACAGATTTGGA | 39 |
| hu107X | C__2570832_10 | ATATTCTAAGTGAAGGAGAGAAAGA[C/T]TTCAAATGTTTGTAAGCATGGAAGA | 40 |
| hu41 | C__3001048_10 | CAGAAATGCTGTGGATATTGACTTA[C/T]CGGACCAAGTTTGGGATGGGCAAGT | 41 |
| hu42 | C_30049893_10 | ACAGGACAGGACAGTTATTCAGGAA[C/T]AGCTTGGGGACAATGCCCCTCCCTA | 42 |
| hu43 | C_11522503_1_ | AAGGCGTTGCAGGAGTTGCCCAGGG[C/T]GTGGGGTCCTCCAGCCTCAGTGAAG | 43 |
| hu44 | C_11673733_10 | GACATTCTCCTTCTTCTATCTGTAT[C/G]CCTTACTGCATTTTGCACTGCAGT | 44 |
| hu45 | C__8263011_10 | GTGTCAATTTTGACCAGATATTAAA[A/T]CTCACAACTCTCTAAACTTCCTTGA | 45 |
| hu46 | C__8844929_10 | AATGCAAATTTCACCTTCTTCAAAT[G/T]TACAACTTTCATGATCAAATTCAAA | 46 |
| hu47 | C__2223883_10 | CTACCTTGGGTCATCAAGATATTTA[C/T]TTTCCTTTTAAATATTTTTCCTACA | 47 |
| hu48 | C__1880371_10 | AGATATATCTTAGATGAAGCAATAG[A/G]GTCAAGAGTAGAAATTTCAGTAGGA | 48 |
| hu49 | C___493379_10 | GATGTCTCATGTACCCCGTAAATAT[A/G]TATACACTTACTGTGTACCCACAAA | 49 |
| hu50 | C__1478361_10 | GCGGCGACGGCAAGGACGACGGTCG[A/G]GCAGCGGCTTCCCGGATCTAGTGCA | 50 |
| hu51 | C_11860358_10 | GAAAGAGCCGGCTCACTTAAGAAAT[A/G]CCAAGTGGTATTACGATGTCACTCC | 51 |
| hu52 | C_29071253_10 | CTTAACATAGTGTTATCATTTTGAT[C/T]CAGCTAAGAGAATTCCACTCCTAAG | 52 |
| hu53 | C_____14517_10 | AAGTTGCAATATGGCAAAACCTGTA[A/G]GAGATACAATTTGTGATTCCACTGA | 53 |
| hu54 | C_27328815_10 | TAATGCACCCTCTCCCTGCTTCTAT[C/T]TTCTGTGCCCATTGCAGCATCAGAC | 54 |
| hu55 | C__2572254_10 | TAAACACAAGATAGAAGCAGACTAG[A/G]CATTTAGCGTTTCCACACAGACGTT | 55 |
| hu56 | C__2140539_10 | AATAATATTTGAACCCTTCAAACAG[A/C]TATGTACACAGGATGCTTGTAGTAT | 56 |
| hu57 | C__8263011_10 | GTGTCAATTTTGACCAGATATTAAA[A/T]CTCACAACTCTCTAAACTTCCTTGA | 57 |
| hu58 | C_12080106_10 | GCCCAGGAACCCAAGGATTGCTTCT[A/G]AAGTCCAAAGAGAGGATTCACGTTC | 58 |
| hu59 | C___411273_10 | AAATCTTGTGTTCATATTTTGCTAT[A/T]TATACCTAACTTTCTCAAGTTGCCT | 59 |
| hu109X | C__2252319_10 | AAGCTCAGAAAGATCCAGAAAGGCC[C/T]GAATGATGGTCCAGAACCAAGACAA | 60 |
| hu61 | C___328256_10 | GAACGGCAGACAAAGCCTCACATTA[A/G]GCATCTCTTTAGTAAAGCATCCAGA | 61 |
| hu62 | C__1519732_10 | GTGAGACAGTTGGACAAGATGATTC[A/G]GGGAATTTTTCAAGCTCAACCAAAC | 62 |
| hu63 | C_29422763_10 | GATGATCTACCTTGCAGGTATAATG[G/T]TTCAAGCATTTGAAAGAGAATCAAG | 63 |
| hu64 | C_16252570_10 | CCTGAAGGTGATGGAAGCCTTGCAT[C/T]TGTGTCTTGGTGCCATGGGGAGCCT | 64 |
| hu65 | C__8340116_10 | TAAGACGGGTTTTTATCAGGACATA[A/G]CCCCCATTGTAAGGAGAGGAGTATC | 65 |
| hu66 | C_27471358_10 | CATAGTGAGGGGTTAGACCTCCATT[C/T]ATTTCAGTCTTTCACAATCTTTGAC | 66 |

TABLE 2-continued

SNPs in Context of Surrounding Sequence.

| RUID | Assay ID | Context Sequence | SEQ ID NO |
|---|---|---|---|
| hu67 | C___342791_10 | CCAAGGGAACGTGAGGAGGCCACAC[A/G]TACAGCTCACCAAACACATCAGCCG | 67 |
| hu68 | C__2997607_10 | ATTAATGTAAAAACTGCAAGTGGTT[C/G]GTGATCAAAACTCCAATGCACATGT | 68 |
| hu69 | C__2450075_10 | TGTCAGCATTTAAAAATAAAACCGA[C/G]TGCCACATTTGCAGAAAAAGAACAA | 69 |
| hu70 | C__7566096_20 | GCATATTCTTAAATCCGTCTTGACT[C/G]AGCTTCATTTGTGAAATGAAGGATT | 70 |
| hu71 | C__2073009_10 | CCCTGCCTCCCACACCAGTTTCTCC[A/G]GAGTGGAAAGACTTTCATCTCGCAC | 71 |
| hu72 | C__2822618_10 | GGTCAAGATATCAGCTTTCACCCGT[A/G]AGGACAGGTTAGTGTTTTTCTTCAA | 72 |
| hu73 | C_30127919_10 | CTCAACAAATAGTGCTAAAATAAAT[C/T]GCTAACCACTGAGGGAAACACAGTT | 73 |
| hu74 | C_27978607_10 | TGGATTCTGTTCTCTTGATGTATTT[G/T]TCTATCTTCACGTCAATACTGCAAT | 74 |
| hu75 | C_30502208_20 | AACACCGGGAGGTCCTTGCAGCTCC[C/T]AGGAAGCAGTTTGCTGATAACTCAG | 75 |
| hu76 | C__2494120_10 | AAGCTTAACCCCTGGGCTATGACAA[A/G]GAGTTGTGACTCCCTCCATTTCTGT | 76 |
| hu77 | C__2938090_10 | GCAGCTATTGCCATTTTTTTCTCAT[A/G]CACAAAATCCTGTATCCTGAGAATG | 77 |
| hu78 | C__1508579_10 | CAGGAGCTTAGGAGAAATAAAATCT[A/G]AATTTCTTTTCAGGAGATGTAAGAG | 78 |
| hu79 | C__1817429_10 | CTAATTTTTCTTATCTTTGTTTTAA[C/T]CTGATGCTTTTTCAAATTCATTCTT | 79 |
| hu80 | C__3254784_10 | CAATGGCTCGTCTATGGTTAGTCTC[A/G]CAGCCACATTCTCAGAACTGCTCAA | 80 |
| hu81 | C__1276208_10 | GATACAGGTTATCTGTATTACATTG[A/G]GTTTTACCTACCTTTCTTGCACAT | 81 |
| hu82 | C_26357333_20 | ATTTCTTTCAGCTCTTGTCATTCAG[G/T]TTAAAGAGAAACCATTTGACATTCT | 82 |
| hu83 | C__7428940_10 | TCTCTTCTCTTCAGTCATCAGAAGC[A/G]TTTAATTACCAGCTTTCTCTAATTA | 83 |
| hu95 | C__1371205_10 | AGAGCAGCACACTGAGGCTTTATGG[A/G]TTGCCCTGCCACAAGTGAACAGGTC | 84 |
| hu84 | C__1386349_10 | CTCTTGTAGACAGGGCCCTCTATCT[A/G]TGTGGTGCATCCTTTATATCTCCAT | 85 |
| hu85 | C__8833162_10 | TCAGTATCTCCAAGTCAGGTCAGGT[C/T]AGGTATGGGACGGATGTGGCAGTGG | 86 |
| hu86 | C__8767011_10 | TCTTGGGGGTCCTGCTCCATGCTGC[A/G]TTACCCCAATCCCCATCCTAAATTA | 87 |
| hu87 | C_30021395_20 | ATGTCACCTTTAGGCAGAGGCATTT[G/T]TATTATTGTTAGTGGAGCTGCTGAG | 88 |
| hu88 | C__2130393_10 | TGAACTGCGCTCCTGGATCTTTTAC[A/G]TAACTGTGGTTTTTCACAAGGTTCT | 89 |
| hu89 | C_11887110_1_ | CACTTAACAGGCTCTCTTTCCACCC[A/T]TGTAGAAATACAAAAATAAGACTTA | 90 |
| hu90 | C_25749280_10 | GACTAAATTGTTGAACACTGGTTAC[C/T]GTGCTAGGTATTTACAAACTTGCTC | 91 |
| hu91 | C__2049946_10 | ATTCCAGATAGAGCTAAAACTGAAG[C/T]TTTCCTTATAGAGATTTATCCTAGT | 92 |
| hu92 | C__2043758_10 | ATTCACTAAACATACATTTGTATTT[G/T]CAGTCTTCTGCTTTATCTTTGGAAA | 93 |
| hu93 | C__7459903_10 | TCACTATATGTTGGCCTTGATTGGT[A/G]TTCCTGAAGTCTTTTGGGCATTTCT | 94 |
| hu94 | C__3153696_10 | TCCAGCCCTTGTCCCAAACGTGTGT[A/G]TGCACAGGCACACGAAAGAAGGTGA | 95 |
| hu96 | C__8948366_10 | CCCAGTTGTCAGCTCTCTGATCTCC[C/T]GCAATCTGGGACTGGTTCCTGAACT | 96 |
| hu113 | C___788020_10 | AATGTGCCCTAGGGCAAGAGAGTAA[A/G]TTCACAGCATGAAGGTATCAATGGA | 97 |
| hu114 | C_16209136_20 | GGTTAAGCAAAAAAGAACAATTAA[A/C]TCACAGTTCAGAGACCTCCAGGAGT | 98 |
| hu115 | C_2618285_30 | AGGTTGGCAGCCACAGCAATAGACT[A/C]CCACTAGAAGTCTAGAAGATGCCCA | 99 |
| hu116 | C_16075644_10 | TTTCTGGATGTGATGACTGGCAATG[C/T]GGCAGCCATTTGAGCCTTAGGGAGC | 100 |
| hu117 | C_27472381_10 | AGGGGTTTGCAGAGGCACAGTGAAA[A/G]AAGGTGCCGAGAAAATAGCAGGGGA | 101 |
| hu118 | C_2968151_20 | ATGCACCATGGCCATTTGGAACTGG[G/T]TAGTGAGAGGCTGCCCTGTCCATTG | 102 |
| hu119 | C___320568_10 | GGTTATCATGGCTGCCCTCTCACTT[C/T]TTCAGAGACATGTGTTTCTAAGGTC | 103 |
| hu120 | C___443622_10 | GATGGCTTAACTCTATAGAAAGGAA[A/G]AGAAGCTCAGCTTATTCATATGCAA | 104 |

TABLE 2-continued

SNPs in Context of Surrounding Sequence.

| RUID | Assay ID | Context Sequence | SEQ ID NO |
|---|---|---|---|
| hu121 | C_9471400_10 | TTACAAAACATTTTTGCATTAGCTT[A/G]AGAAGGATAAACCAATTCCATGCTG | 105 |
| hu122 | C__9583289_10 | AGCCAAGAAGCCAAGGACAGCTAAT[G/T]CTTAGCACCTGGTTACAGATGCCTC | 106 |

The methods of the present invention have broad applications for both the scientific and service community with respect to standardizing DNA quality and functional measurements for large scale genetic studies. Also provided is a data resource having tools for analysis that allow for a comprehensive, real time assessment of DNA quality and performance for a sample within and across studies. The combination of the two components of assay development and data analysis tool constitutes a unique product having commercialization value and multiple downstream applications.

In one aspect, the present invention provides a collection of SNP containing nucleic acids as genetic markers which can be used to advantage to ensure DNA quality and uniqueness. The collection can be used for determining gender, ethnicity, DNA quality and uniqueness of a biological sample. In certain embodiments, the genetic markers are single nucleotide polymorphisms (SNPs). In more particular embodiments, the collection of genetic markers comprises the first 96 or all 106 SNPs presented in Table 1, where each SNP is identified by a RUID number as well as the National Center for Biotechnology Information (NCBI) database SNP (dbSNP) number. The 96 or 106 SNPs presented in Table 1 are shown in context of their respective surrounding nucleic acid sequences in Table 2, represented by the nucleic acid sequences of SEQ ID NOs: 1-106. In some embodiments, the collection of genetic markers is a subset of the first 96 SNPs set forth in Table 1 and comprised within the nucleic acid sequences of SEQ ID NOs: 1-96 as set forth in Table 2. In particular embodiments, the subset comprises at least 5 of the 96 SNPs comprised within the nucleic acids of SEQ ID NOs: 1-96 as set forth in Table 2. In another embodiment all 106 are employed.

The collection of SNP containing nucleic acids of the invention can be provided in a number of formats, including but not limited to, as a list of the nucleotide sequences encoding or comprising the nucleic acid sequence reflective of the marker, on a computer readable storage medium, and physically affixed to a solid support. For example, in a collection of SNPs, sequences of SNP-containing nucleic acids are provided in a list or stored on a computer readable storage medium, or SNP-containing nucleic acids are physically affixed to a solid support.

In some embodiments, a subset of the 106 SNPs, are provided in a list or compilation or are assembled or stored in a computer medium. In some embodiments, such subsets are physically affixed to a solid support, in the form of, for example, a microarray. Finally, in alternative embodiments, the biological sample can be assessed for additional SNP markers in order to more fully characterize the genetic and phenotypic nature of the sample.

Quality and integrity are reflected by a number of detectable characteristics of the sample. Issues of importance and concern to a biorepository that collects or acquires, processes, stores, distributes and analyzes large numbers of biological nucleic acid containing samples are sample degradation, gender misidentification or mismatches, ethnicity misidentification or mismatches, sample contamination, sample mislabeling, errors in data capture. The methods of the present invention allow for the detection of problems with regard to the quality and integrity of a nucleic acid sample by examination of particular genetic markers in the sample. In particular embodiments, markers reflective of gender and/or ethnicity and/or uniqueness are used to detect discrepancies with input information about a sample. In particular embodiments, the methods of the invention are used to confirm the gender and/or ethnicity of the source of the nucleic acid sample. In another approach, the methods of the invention are used to ascertain or confirm whether a nucleic acid sample has been contaminated with, for example, a sample from another source, mislabeled, or whether data or information associated with a particular nucleic acid sample has been improperly or incorrectly recorded.

In one method for assessing the quality and integrity of a nucleic acid sample, the sample is analyzed to determine the genotype at one or more genetic loci. In particular embodiments, the genotype of one or more or all of the SNPs in the panel of 96 SNPs of the invention is determined for a sample. In particular embodiments, samples are analyzed to determine the SNP genotype for all 106 SNPs in the panel or for a subset of the 106 SNPs. Genotype information, in particular SNP genotype information, for a sample can be stored (e.g., in a computer readable medium) and compared to the genotype information for another sample or samples. Many methods for determining a SNP genotype for a nucleic acid sample are known to those of skill in the art, including dynamic allele-specific hybridization (DASH) genotyping, SNP detection through molecular beacons using specifically engineered single-stranded oligonucleotide probes, and other sequence analysis methods know to the art, including, but not limited to, polymerase-mediated enzymatic methods such as Sanger dideoxy sequencing, sequencing by hybridization, direct linear analysis, nanopore sequencing, polynucleotide chain reaction (PCR)-based methods, such as quantitative polymerase chain reaction (QPCR), direct sequencing, and tandem mass spectrometry. In particular embodiments, SNP genotyping is carried out using TaqMan probes, relying on the 5'-3' nuclease activity of Taq polymerase to cleave a dual-labeled probe during hybridization to the complementary target sequence and fluorophore-based detection, in a system such as a Fluidigm BioMark™ genotyping system.

In particular embodiments, a sample is subjected to sequence analysis or SNP genotyping of the loci represented by the entire collection or a subset of the 106 SNP-containing nucleic acids of SEQ ID NOs: 1-106 or fragments thereof. This sequence analysis will identify the genotype at each locus examined (the genotype for each SNP) for the sample. This collected sequence information around all the loci examined, for each sample is also referred to herein as a "SNP fingerprint". In particular embodiments, the genotype information is stored in a computer readable medium so that it can be compared to previously collected or known information about the sample, or to the SNP genotype or sequence information of another sample or samples in a database.

In some embodiments of the invention, a sample will be genotyped for the full collection of 106 SNPs to determine nucleic acid sample quality and integrity. In some embodiments, a sample is genotyped for a subset of the 106 SNPs. In particular embodiments, the subset comprises at least 5, at least 10, at least 20, at least 30, at least 40, at least 50, or at least 75 of the 106 SNPs. In particular embodiments, information about the gender of the source of the nucleic acid sample is revealed and/or confirmed by genotyping for the subset of SNPs hu98Y, hu103X, hu106Y, hu107X, hu109X and hu111Y (SNPs contained within SEQ ID NOs: 6, 19, 8, 40, 60 and 10, respectively). In particular embodiments, information about the ethnicity of the source of the nucleic acid sample is revealed and/or confirmed by genotyping for the subset of SNPs hu1, hu2, hu4, hu5, hu9, hu11, hu13, hu14, hu15, hu16, hu17, hu18, hu20, hu21, hu23, hu25, hu26, hu27, hu29, hu30, hu31, hu32, hu33, hu34, hu35, hu36, hu37, hu38, hu39, hu41, hu42, hu49, hu50, hu52, hu53, hu54, hu55, hu58, hu59, hu61, hu62, hu63, hu64, hu66, hu69, hu71, hu72, hu73, hu74, hu75, hu76, hu77, hu78, hu79, hu83, hu85, hu86, hu87, hu88, hu90, hu91, hu92, hu94 and hu96. In particular embodiments, information about the uniqueness of the nucleic acid sample and/or the source of the nucleic acid sample is revealed and/or confirmed by genotyping for the subset of SNPs that are highly polymorphic, SNPs hu7, hu12, hu22, hu24, hu43, hu44, hu45, hu46, hu47, hu48, hu56, hu57, hu67, hu68, hu70, hu80, hu82, hu89 and hu95. In particular embodiments, information relating to sample contamination or sample mislabeling is revealed and/or confirmed by genotyping for the entire panel of 106 SNPs or a variety of subset panels of SNPs. For example, genotyping for the subset of gender related SNPs may be sufficient to reveal a sample mislabel relating to the gender of a sample source.

In the methods of the present invention, algorithms are used to determine nucleic acid sample quality and integrity. Such algorithms reveal information about uniqueness of a sample, performance (or quality) of the sample and/or the nucleic acid of the sample, gender of the source of the sample, or ethnicity of the sample. As mentioned above, "call" or "calls" refers to genotype assignment or designation of a particular characteristic to a sample. For example, in genotype calling related to SNPs, a genotype "call" or assignment is made (i.e., AA, AB or BB genotype for the two alleles). If the intensity value of a SNP is not high enough for detection, its score falls outside the boundaries of the statistical model being used for the analysis, or the quality of the nucleic acid in the sample is poor, a "no call" value can be assigned for a particular SNP for a particular sample.

Uniqueness

One function of the RUID QC database is to determine whether or not an individual sample has an identical SNP fingerprint with any other sample or samples in the database which would indicate sample contamination, sample mishandling, or errors in sample registration (in the absence of monozygotic twins). To this end, the algorithm used for determining sample uniqueness is as follows.

A) Any samples that have the same RUID and have distinct profiles (i.e., samples that are supposed to be the same but that have different SNP fingerprints) are evaluated based on "no calls" to determine if the call rate leads to this identification. In other words, samples which "pass" performance criteria are compared to ensure that the fingerprint is not the same across two separate individuals, or that the samples are not just different sources of DNA from the same individual. Any sample that has one "no call" or one discrepant SNP is passed and all other samples are failed.

B) Any sample that has an identical profile to another sample is called a "match with other RUID" category. Only samples that "pass" the performance algorithm (see herein below) are evaluated in this analysis (by default). Any samples with "multiple distinct profiles" or "match with other RUID" are checked for gender discrepancies followed by correlation to sample registration information. In the event the relatedness of a given sample is known (i.e., family collection), a parentage analysis is performed to determine the likelihood of the sample being related. In case there are multiple sources of DNA, the primary samples are functionally evaluated to determine if laboratory procedures contributed to the result. Through this decision matrix most sample matches are proactively resolved.

Performance

Nucleic acid quality (for example, DNA quality) is a metric determined by analysis with the RUID QC panel. All assays are allelic discrimination assays which cover the autosome allowing for analysis with respect to ability to purify across a region on each chromosome. Considering that every individual has an X chromosome, the total number of SNPs are "gender" adjusted prior to performance analysis. If more than 2 SNPs fail to provide signal/cluster call then the sample is deemed a failure due to poor performing nucleic acid (DNA). The decision of 2 SNP failures as cut off for performance was determined empirically after the evaluation of over 10000 individual DNA samples from a variety of sources (Whole Blood (WB), Lymphoblast Cell Lines (LCL), Cryopreserved Lymphocytes (CPL), Whole genome amplified DNA (WGA), Blood Spot Card DNA (BSC), Saliva DNA (S), Plasma DNA (P), Serum DNA (SE)).

Gender

Calls for gender are made as follows.

A sample is identified as "male" (a male call) if

A) all X (all of the X SNPs (hu103X, hu107X and hu109X)) and all Y (all of the Y SNPs (hu98Y, hu106Y and hu111Y)) calls are made for a given sample;

B) all X and at least two Y calls are made for a given sample; or

C) two X calls are made and all Y calls are made for a given sample.

A sample is identified as "female" (a female call) if

A) no Y calls are made and all X calls are made for a given sample; or

B) no Y calls are made and at least two X calls are made for a given sample

No Gender Call or 'No Call" is made if there is only one call made out of three possible calls for X or Y assays.

Figure 2A:
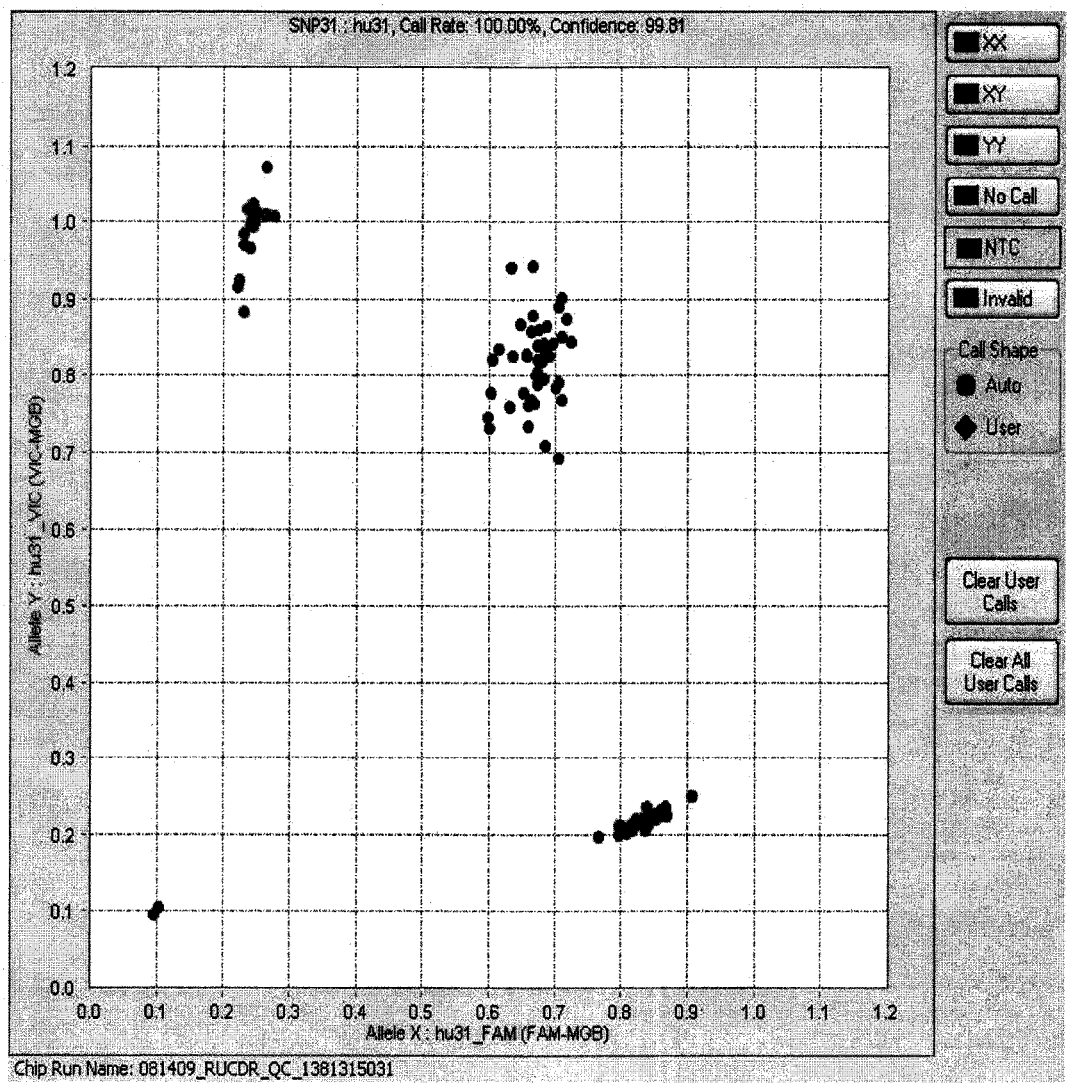
FIGS. 2A and 2B are screenshots of the profile analysis screen.
Figure 2B:
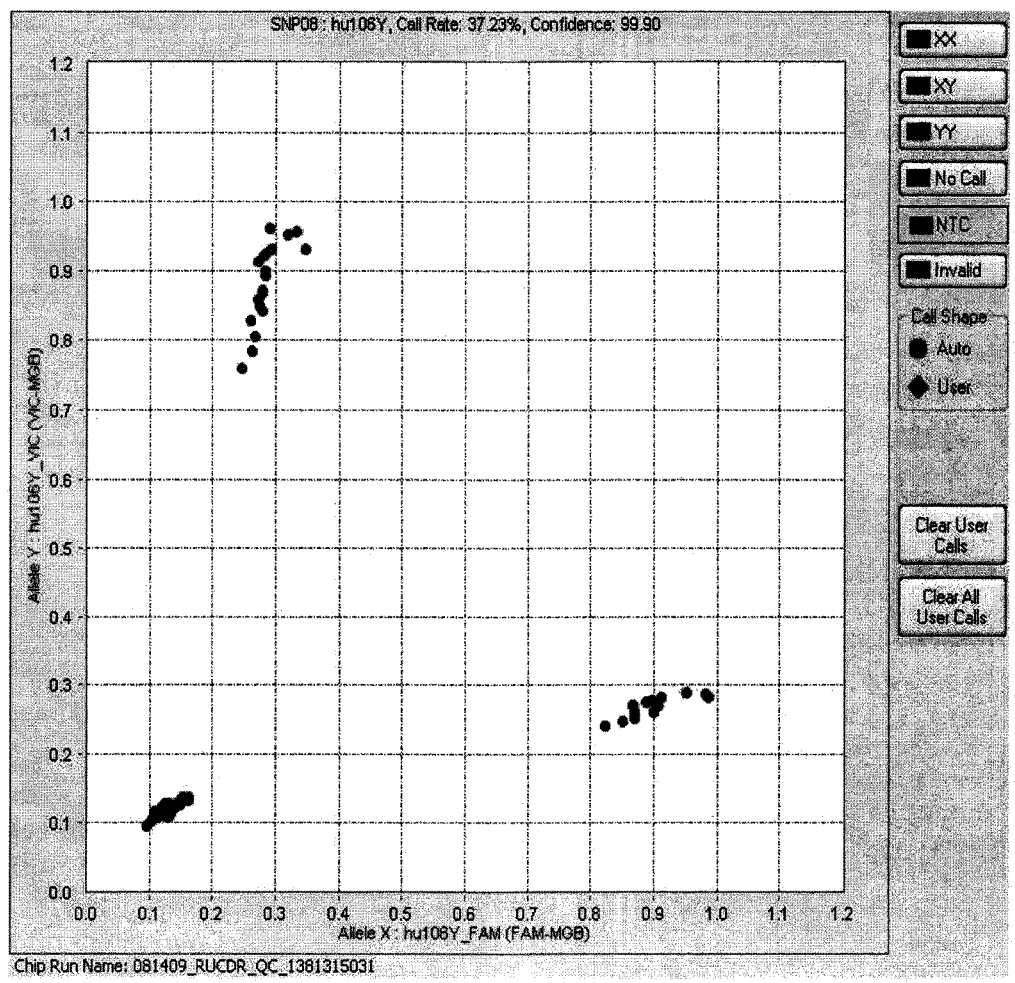

FIG. 2 shows an array of gender determination using the hu106Y SNP.

Ethnicity

Calls for ethnicity are described, for example, in Seldin et al., 2008, PLoS Genetics, 4:e5 The panel of 96 SNPs of the present invention includes 64 SNPs that are informative of ethnicity. Kosoy et al. present methodology for using relatively small subsets of ancestry informative marker (AIM) SNPs to assess and compare ancestry in large numbers of samples (Kosoy et al., 2008, Human Mutation, 30:69-78).

In another aspect, the present invention provides a computer program that carries out the analyses used in the methods for the invention.

In another aspect, the present invention provides a database comprising the sequences of the SNP-containing nucleotide sequences of the collection of genetic markers of the invention and/or the sequence information obtained using the methods of the invention.

The following examples are provided to illustrate various embodiments of the present invention. The examples are illustrative and are not intended to limit the invention in any way.

EXAMPLE I

DNA Quality Control/Quality Assurance Workflow

In addition to implementing the Fluidigm BioMark™ genotyping system for high-throughput SNP analysis on all samples, we have updated the entire sample handling process for managing DNA in the RUCDR. All essential components of sample handling including: extraction, aliquoting, storage format, analytical measurements, and the addition of functional analysis through SNP genotyping have been modified/added and validated in the DNA workflow.

DNA handling and quality control workflows are illustrated in FIG. 1. At each critical stage in the process there has been a significant technological improvement. All sample handling is now performed on liquid handling instrumentation. The Micronic 2D tube rack system has been implemented for all nucleic acid storage. High-throughput precision spectroscopy has been implemented to preserve precious sample and improve measurement accuracy. Non-contact volume measurements have been added to all storage tubes with an accuracy of +/−3 Qualitative, quantitative and functional measurements are being performed (in place of basic gel analysis) via a 96 or 106 SNP panel that generates information on sample uniqueness, gender and ethnicity. This data is managed in a custom database to allow for the management of all QC data.

Assay/Workflow Performance

Figure 3A:
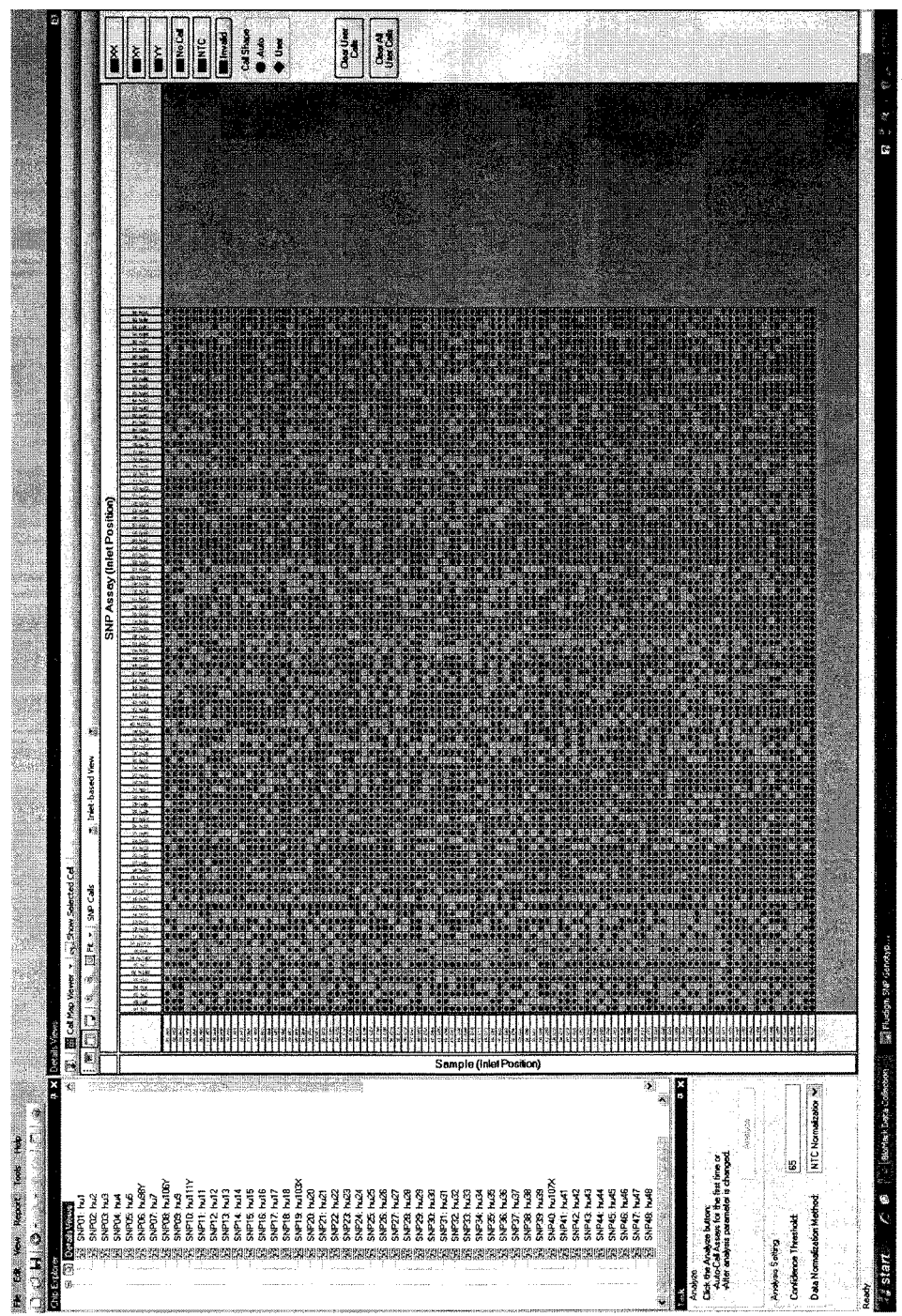
FIGS. 3A and 3B present the illustration of assay performance on the Fluidigm BioMark™ system 96.96 microfluidic arrays.
Figure 3B:
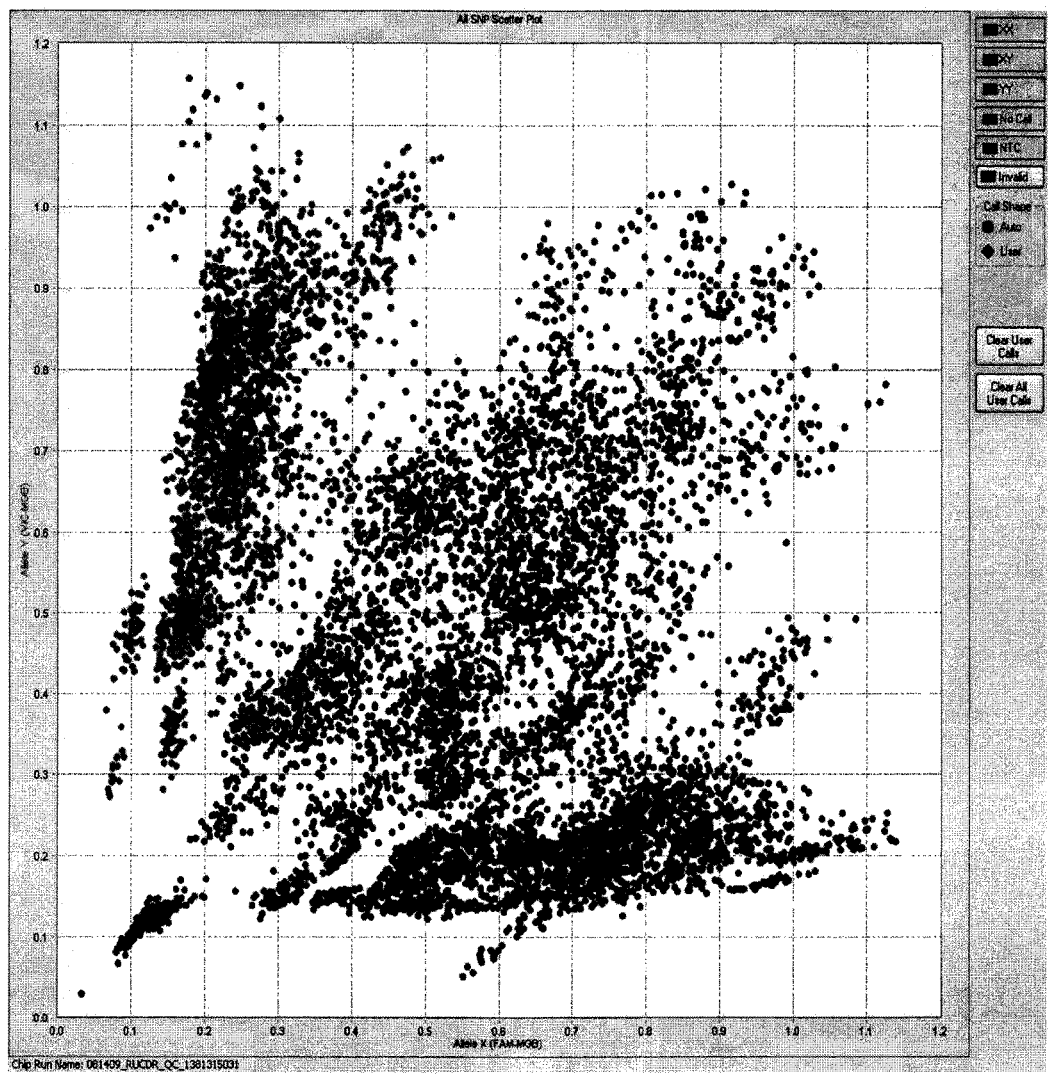
Figure 4A:
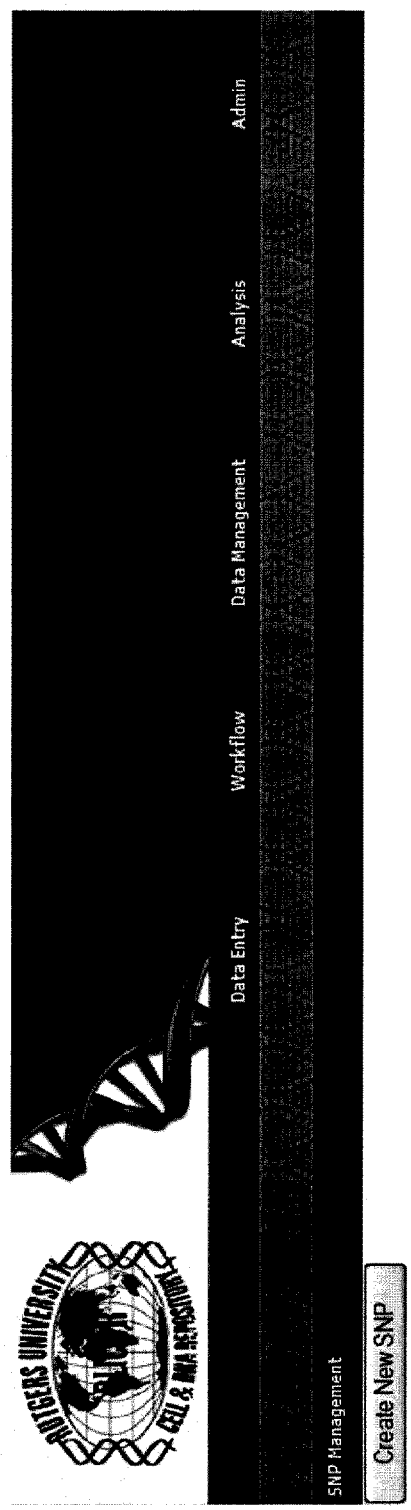
FIG. 4 depicts Data Management and Analysis via the RUCDR DNA QC Database. (A) SNP panels are created within the database to accommodate specific analyses. (B) Samples are held in quarantine until analysis is completed by the database. All information about sample project and ID are recorded in the database. (C) Samples are analyzed for SNP performance, gender, and ethnicity immediately following data upload. Failed samples are reported and repeated immediately prior to the automated query for sample uniqueness. (D) Every profile in the QC database is compared against all other samples in the database to determine uniqueness of every sample, irrespective of source and project.
Figure 4B:
Figure 4D:

In order to transition from standard QPCR applications using allelic discrimination for genotyping, each assay in the QC panel needed to be validated on the Fluidigm BioMark™ genotyping system prior to implementation. Over 5000 samples were run on both platforms which resulted in a 100% concordance for the new QC workflow. The process component of this new workflow improved laboratory efficiency by 40% and sample accuracy by 20%. This is primarily a function of automated sample handling; a 90% reduction in manual pipetting. See also FIGS. 3A and 3B for assay performance with 9200 genotypes.

Data Management and Analysis

The implementation of a QC SNP panel has resulted in and will continue to generate millions of data points across the >100,000 unique new sample receipts in the RUCDR annually. In order to fully utilize the rich data resource for quality control analysis, a relational database scheme has been created to manage and analyze data generated directly from the Fluidigm BioMark™ 48.48 and 96.96 Dynamic microfluidic arrays. All aspects of data management and analysis, including but not limited to, panel registration, sample registration/upload, performance analysis, gender determination, ethnicity assignment, and, most importantly, the analysis of sample identity across all other samples in the database have been included in the RUCDR DNA QC Database (see FIGS. 4A-D). This computationally intensive task results in the identification of samples that need attention due to potential: sample contamination, gender discrepancy, cell line contamination and sample registration errors at the time of collection. The RUCDR DNA QC database immediately identifies all samples that are not unique.

Conclusion

We have employed novel technologies to fully automate the DNA workflow process leading to improved processing, storage and analysis of all samples in the RUCDR. Efficiency of sample handling and storage has collectively led to an operational improvement of >80% for RUCDR nucleic acid workflows. Implementation of a 96 SNP panel for DNA quality assurance/quality control (QA/QC) via the Fluidigm BioMark™ genotyping system has led to detailed functional analysis of all clinical samples in the RUCDR. Development of the RUCDR DNA QC database allows for the real time assessment of sample quality and characterization leading to improved operational efficiency.

EXAMPLE 2

Using Single Nucleotide Polymorphisms for Identity Testing

There are around 10 million single nucleotide polymorphisms (SNPs) in the human genome. Being biallelic (i.e., a locus at which there are two possible variations of a given DNA sequence that are detectable in the population), they are much easier to type than other polymorphic markers such as short tandem repeats (STRs). Thus, there is a great deal of interest in using SNPs for human identification. Some of the applications and questions that can be answered include:

Identity Testing:

What is the probability that two unrelated individuals will have the same genotypes at one or more loci?

Parentage Testing:

What is the probability that an alleged parent from the same ethnic/racial background as the biological parent is the biological parent?

Ancestry Testing:

What is the probability that one or more individuals descended from a common ancestor?

Identity testing requires examination of alleles that are common in the population under study, so that individuals can be easily identified using a relatively small number of loci. The converse is true for parentage and ancestry testing, where allele frequencies need to be very different in the populations under study, so that rare relationships can be identified.

We have evaluated the utility of the 96 SNP panel disclosed herein for identity testing (determining the probability that two unrelated individuals have the same genotype). We made the following assumptions.

1. For a biallelic system, the frequencies (p and q) of two alleles (A and B) at a given locus are equal, so that $p=q=0.5$.
2. The population is in Hardy-Weinberg equilibrium, so that genotype frequencies can be calculated from the allele frequencies.
3. The inheritance of any one allele is independent of the inheritance of any other allele.

Given that $p=q=0.5$, the genotype frequencies are $p^2$, $q^2$, and $2pq$.

$p^2=(0.5)^2$, $q^2=(0.5)^2$, and $2pq=2$ $(0.5\times0.5)$, thus
$p^2=0.25$, $q^2=0.25$, and $2pq=0.5$ The probability of two individuals having the same genotype at a given locus is the square of the individual probabilities:

$$(0.25)^2+(0.25)^2+(0.5)^2=0.065+0.065+0.25=0.375$$

This is the same as 1/2.667 (1/0.375). Thus, the probability that two unrelated individuals will have the same genotype at a given biallelic locus is approximately 1 in 3.

Our 96 SNP panel has 6 loci that can be used to determine gender. Once gender has been verified using these loci, the remaining 90 loci can be used to determine the probability of identity for two individuals having the same gender. Thus, the gender loci should not be used in the identity calculations.

For example, for 10 independent loci, the probability of identity is $(0.375)^{10}=5.499^{-5}$, which is the same as 1 in 18,185 (1/5.499$^{-5}$), or 1.8×10$^4$. For 90 loci, the probability of identity is $(0.375)^{81}=3.137^{-35}$, which is the same as 1 in 3.2×10$^{34}$ (1/3.137-35).

Thus, using a panel of 81 SNP loci, the probability that two unrelated individuals of the same gender will have the same genotypes is 1 in 3.2×10$^{34}$.

However, one issue with the above calculation is that it includes the SNP markers that have been selected for ethnicity. The frequencies (p and q) of the two alleles for each of these SNP markers are not likely to be 0.5. In addition, these markers may not be inherited in an independent manner. Thus, the above calculations, using all 81 SNPs, may not be valid.

Assuming there are 64 ethnicity markers, and we remove some of those from the calculation, as they are not as highly polymorphic, this would leave 50 markers for identity testing. The probability of identity using this number of markers=$(0.375)^{50}=5.030\times10^{-22}$. This is the same as 2.0× 10$^{21}$. For comparison, the current world population is around 6.7×10$^9$.

EXAMPLE 3

Sample Validation

Routine sample validation is one of the primary applications of the RUID panel and RUID QC database. At the time of data upload the 106 SNP calls from each individual sample is compared across every other sample in the database to determine whether or not that specific combination of 106 SNP calls is present. In the event that the DNA is from two different individuals (irrespective of DNA source) then the analysis returns a result that confirms the uniqueness of the sample. This approach is used routinely to A) make sure that subjects do not register in multiple studies, B) make sure that all cell lines generated in the RUCDR "match" the DNA from the original whole blood sample from which they were derived, and C) confirm the genetic relatedness of two individuals. At the completion of every data upload the performance and comparison analysis of the newly uploaded samples is used to categorize every sample in the RUCDR.

EXAMPLE 4

Analysis of gDNA from Monozygotic Twins

Recently the RUCDR was contracted by the NIMH to manage the Netherlands Twins Registry (NTR) collection. This collection of monozygotic, dizygotic and non-twin pair family members is being used to study a variety of psychiatric disorders with a focus on identifying the genetic component of complex disease states. The RUID panel is being used to confirm family membership, and more importantly, to validate the status of monozygotic twins given the "identical" nature of their genetic makeup. The matches identified by the RUID panel confirmed the registry of monozygotic twins in a collection of over 10,000 individual clinical samples.

EXAMPLE 5

Gender Mismatch

All biorepository programs will often have the problem of sample registration errors at the time of collection. One of the easiest ways to immediately identify sample "mix up" issues early on, is through gender mismatch determination. The RUID panel provides an immediate and robust gender call for every DNA sample, allowing for a real time reconciliation of reported gender on the sample registration sheet, which allows the repository data manager to decipher mislabeling and incorrect sample assignments very early on in a study. Traditional analysis of DNA for quality assessment lacks the ability to provide useful genetic information for each sample for a priori identification of sample registration errors.

EXAMPLE 6

Genome Wide Association Study (GWAS) Validation

One of the primary downstream applications of DNA stored in central biorepositories is their inclusion in genome wide analysis studies which are inherently expensive and time consuming. The RUID panel is employed to validate that the correct DNA is used and that the quality of the GWAS is commensurate with the effort employed on the analysis. The RUID panel is also used to validate the sources of the samples to prevent adversely affected conclusions from these large scale studies. Because greater than 80% of the SNPs in the RUID panel are the "same" as the SNPs on the major commercial platforms being employed by commercial array manufacturers, the results from the RUID panel are the primary source of sample validation prior to detailed analysis of genome wide association studies.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting a collection of genetic markers in a sample, comprising, providing a sample comprising DNA, wherein the DNA comprises a collection of genetic markers, and wherein the sample is selected from the group consisting of a blood sample, a serum sample, a plasma sample, a lymphoblast cell line (LCL) sample, a cryopreserved lymphocyte (CPL) sample, a cell line, a tissue sample, a frozen tissue sample, a whole genome amplified DNA sample, and a saliva sample, contacting the sample with a polymerase and a panel of nucleic acid molecules that can detect a collection of genetic markers consisting of SEQ ID NOS: 1-96, amplifying the DNA in the sample, and detecting one or more single nucleotide polymorphisms (SNPs) present in said collection of genetic markers, thereby genotyping the sample, wherein detecting SNPs in the collection of genetic markers using the panel of nucleic acid molecules that can detect a collection of genetic markers consisting of SEQ ID NO: 1-96 demonstrates an improved ability to reliably genotype the collection of genetic markers in the sample as compared to other combination of nucleic acid molecules.

2. The method of claim 1, wherein the nucleic acid molecules that can detect a collection of genetic markers consisting of SEQ ID NOS: 1-96 comprise dual labeled probes, and the polymerase cleaves said dual labeled probes during hybridization to a complementary target sequence present in said sample, wherein the dual labeled probes comprise a fluorophore.

3. The method of claim 2, wherein said cleavage releases the fluorophore.

4. The method of claim 1, wherein said detecting is performed using an array comprising the collection of genetic markers consisting of SEQ ID NOS: 1-96.

5. The method of claim 1, wherein a genotype assignment has been previously determined for the sample, said sample being stored in a biorepository.

6. The method of claim 1, wherein the DNA is selected from the group consisting of genomic DNA (gDNA), complementary DNA (cDNA), free floating DNA, and recombinant DNA.

7. The method of claim 1, wherein the sample is a human blood sample.

8. The method of claim 1, wherein the sample is a human serum sample.

9. The method of claim 1, wherein the sample is a human plasma sample.

10. The method of claim 1, wherein the sample is a human saliva sample.

11. The method of claim 1, wherein the sample is a human tissue sample.

12. The method of claim 1, wherein the sample is a blood sample.

13. The method of claim 1, wherein the sample is a serum sample.

14. The method of claim 1, wherein the sample is a plasma sample.

15. The method of claim 1, wherein the sample is a saliva sample.

16. The method of claim 1, wherein the sample is a tissue sample.

17. The method of claim 1, wherein the amplifying comprises polymerase chain reaction (PCR).

18. The method of claim 15, wherein the PCR comprises quantitative polymerase chain reaction (QPCR).

19. The method of claim 1, wherein the detecting comprises sequencing.

* * * * *

UNITED STATES PATENT AND TRADEMARK OFFICE
CERTIFICATE OF CORRECTION

PATENT NO. : 9,938,575 B2
APPLICATION NO. : 13/814619
DATED : April 10, 2018
INVENTOR(S) : Jay A. Tischfield and Andrew I. Brooks It is certified that error appears in the above-identified patent and that said Letters Patent is hereby corrected as shown below:

In the Specification

Column 1, Lines 10-12:
"The United States government has rights in this invention which was made using funds from NIH Grant No. 5U24MH068457."

Should read:
--This invention was made with government support under grant number MH068457 awarded by the National Institutes of Health. The government has certain rights in the invention.--

Signed and Sealed this
Second Day of June, 2020

Andrei Iancu
*Director of the United States Patent and Trademark Office*